United States Patent
Castro et al.

(10) Patent No.: US 9,551,560 B2
(45) Date of Patent: Jan. 24, 2017

(54) EXTENSOMETER REMOTE ARM ACTUATION

(71) Applicant: ILLINOIS TOOL WORKS INC., Glenview, IL (US)

(72) Inventors: Fernando L. Castro, Westwood, MA (US); Peter Tsiomplikas, Taunton, MA (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 100 days.

(21) Appl. No.: 14/424,484

(22) PCT Filed: Sep. 5, 2013

(86) PCT No.: PCT/US2013/058337
§ 371 (c)(1),
(2) Date: Feb. 27, 2015

(87) PCT Pub. No.: WO2014/039728
PCT Pub. Date: Mar. 13, 2014

(65) Prior Publication Data
US 2015/0204646 A1    Jul. 23, 2015

Related U.S. Application Data

(60) Provisional application No. 61/697,624, filed on Sep. 6, 2012.

(51) Int. Cl.
G01B 5/30 (2006.01)
G01B 7/16 (2006.01)
G01N 3/06 (2006.01)
F16H 37/12 (2006.01)

(52) U.S. Cl.
CPC .............. *G01B 5/30* (2013.01); *F16H 37/122* (2013.01); *G01B 7/16* (2013.01); *G01N 3/062* (2013.01)

(58) Field of Classification Search
USPC ..................................... 33/787, 790
See application file for complete search history.

(56) References Cited

U.S. PATENT DOCUMENTS 2,085,687 A    6/1937    Peters
2,663,085 A *  12/1953    Ruge ........................ G01B 5/30
                                                 33/787

(Continued)

FOREIGN PATENT DOCUMENTS

CN    2116899 U    9/1992
CN    2164015 Y    5/1994

(Continued)

OTHER PUBLICATIONS

ISR and WO for PCT/US2013/058337 mailed Nov. 11, 2013.

*Primary Examiner* — Christopher Fulton
(74) *Attorney, Agent, or Firm* — McCarter & English, LLP

(57) ABSTRACT

The disclosure relates to an extensometer wherein the actuation of the contact arms is performed by a separate rotating bar so as to avoid or minimize placing active mechanics onto the arms. The rotating bar includes a spool about which a metal belt is wound. Rotating the bar, and hence the spool, in the desired direction pulls the metal belt which pulls a spring-loaded wedge with internal camming slots which urges the contact arms apart.

20 Claims, 25 Drawing Sheets

(56) References Cited

U.S. PATENT DOCUMENTS

| | | | | | |
|---|---|---|---|---|---|
| 2,827,705 | A | * | 3/1958 | Elliott | G01N 3/06 33/560 |
| 4,315,372 | A | * | 2/1982 | Kinkead | A61B 5/0053 33/798 |
| 4,823,473 | A | * | 4/1989 | McMahon | G01B 5/30 33/787 |
| 4,848,161 | A | * | 7/1989 | van der Kuur | G01B 7/16 33/501.6 |
| 5,819,428 | A | * | 10/1998 | Meyer | G01B 7/16 33/787 |
| 5,899,910 | A | * | 5/1999 | Etman | A45D 26/0076 606/133 |
| 6,910,402 | B2 | * | 6/2005 | Drzewiecki | E21B 19/164 81/57.17 |

FOREIGN PATENT DOCUMENTS

| | | |
|---|---|---|
| CN | 201096687 Y | 8/2008 |
| CN | 201740701 U | 2/2011 |
| JP | 61-130849 A | 6/1986 |
| JP | 2000-234904 A | 8/2000 |

\* cited by examiner

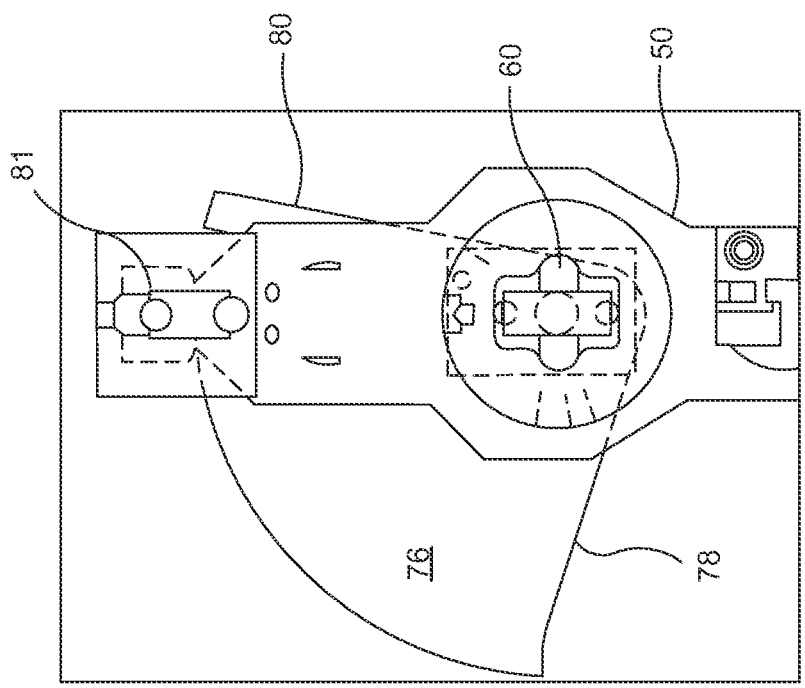
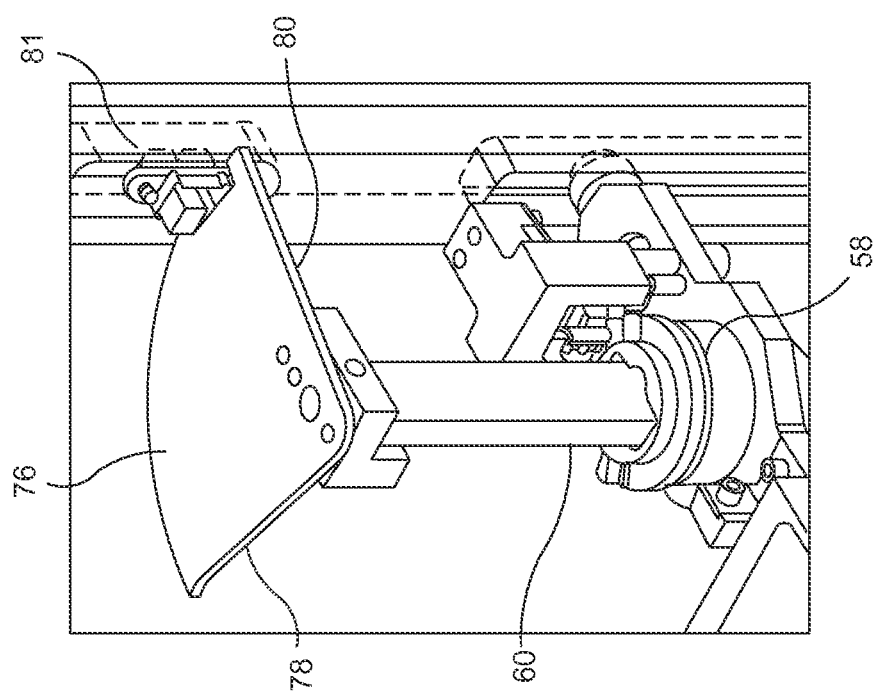
FIG. 9B
FIG. 9A

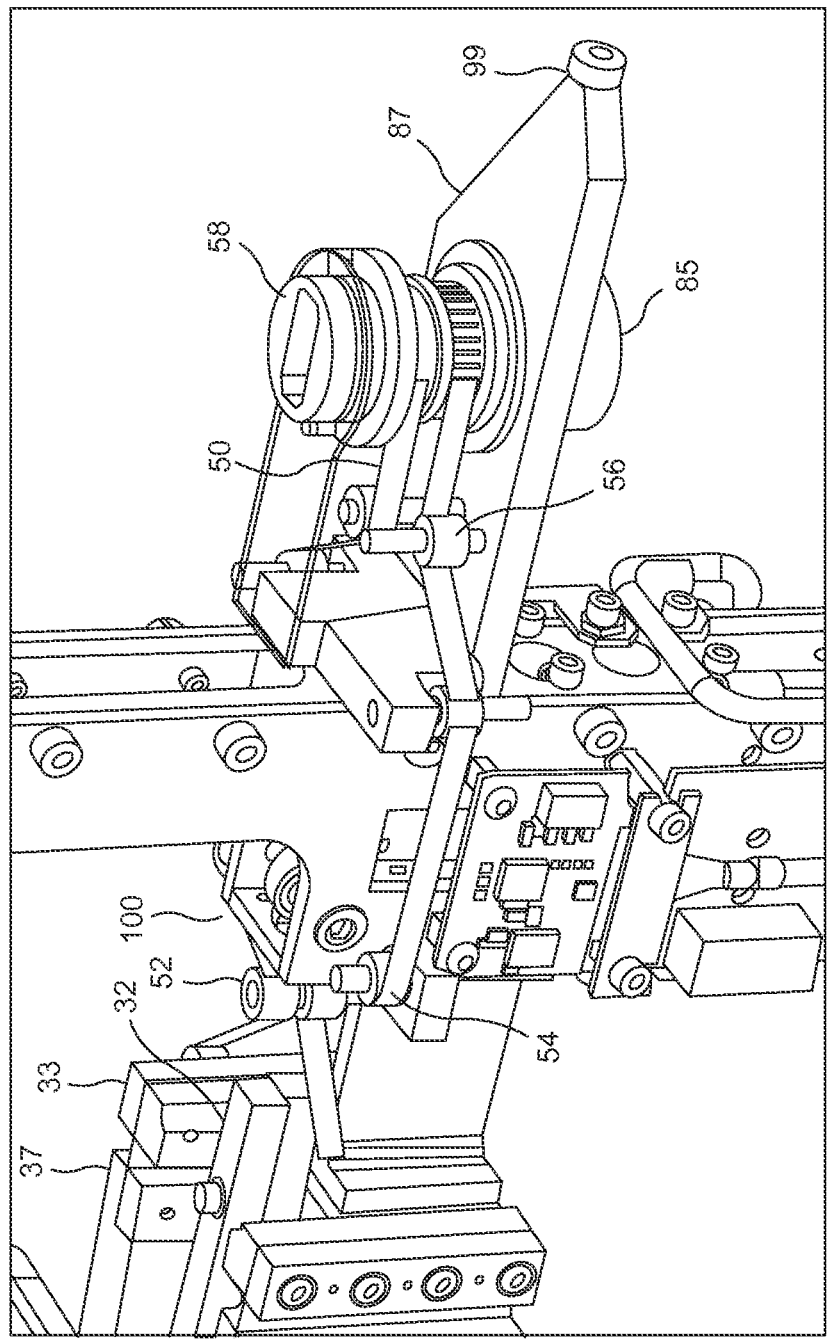
F I G. 13

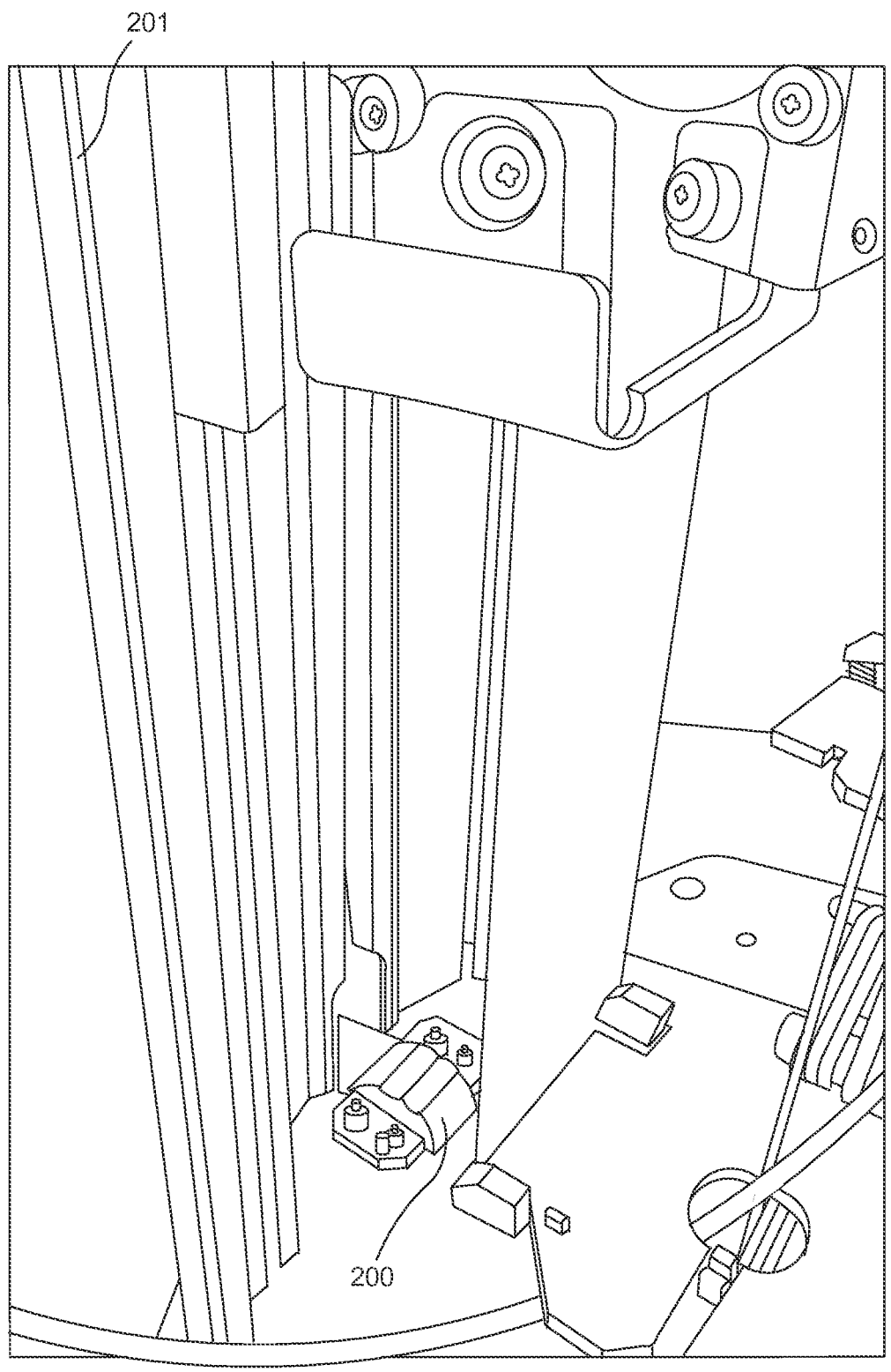
F I G. 22

EXTENSOMETER REMOTE ARM ACTUATION

The present application claims priority under 35 U.S.C. 119(e) of provisional application Ser. No. 61/697,624, which was filed on Sep. 6, 2012, the contents of which are hereby incorporated by reference in their entirety.

BACKGROUND OF THE DISCLOSURE

Field of the Disclosure

The present disclosure relates to an extensometer wherein the actuation of the arms is performed by a separate rotating bar.

Description of the Prior Art

An extensometer is an instrument that very accurately measures the extension of a test specimen in order to better capture the material properties of the specimen. A common extensometer is of the contacting type, which physically tracks two points in the specimen as the test takes place. These contacting points are typically in the form of arms that reach from the main body of the extensometer to the specimen location.

For automatic contacting extensometers, it is necessary to have a means to make the contacting arms attach to and detach from the test specimen. Existing products make use of actuators, usually electric motors that are mounted to each of the two moving arms.

During a test, the load cell on a test frame measures the force that is applied to the specimen. Since the arms are contacting the specimen, the load cell output will include not just the force applied to the specimen but also the additional force required to move the contacting arms. The force required to move these arms is called the running force. The running force also causes the contacting arms to deflect, causing errors in the extensometer readings. For these reasons, minimizing the running force is crucial to load output accuracy and extension accuracy.

The idea of an external bar being used to remotely actuate the arms has been used before in an extensometer, notably the MFL by Mess & Feinwerktechnik (MF) shown on FIG. 1. The device in FIG. 1 does not use a linear encoder to measure the displacement of the arms.

The actuation method employed in FIG. 1 is based on the use of two eccentrically-mounted shafts that operate in a cam-action as shown in FIG. 2. Driven from a common actuator shown in FIG. 3, the cam bars move synchronously until the high point rotates into contact with a tab on each arm of the arm pair, forcing the arms open as shown in FIG. 4.

Another prior art approach is to have a system where sensitive strain gauges are attached to the ends of the arms. The device then lets the strain gauges track the displacement of the specimen until the end of the very limited travel of the strain gauges is about to be reached, at which point the instrument uses actuators to move the arms in the direction of specimen elongation to provide slack and allow more strain gauge travel. As a result, this architecture is immune to increased friction. The arm location is driven by motors even during testing, and not by the specimen itself.

SUMMARY OF THE DISCLOSURE

The disclosure allows the actuation of the arms to be removed from the arms by use of a separate rotating bar so as to avoid or minimize placing active mechanics onto the arms. The disclosure overcomes many challenges and successfully packages the mechanism fully inside the instrument, resulting in many advantages. Many of the typical advantages are the result of implementing the rotating bar inside the unit, with a unique method of transferring the rotational motion of the bar located in the back of the extensometer, yet actuating the arms which are located in front and outside of the instrument.

BRIEF DESCRIPTION OF THE DRAWINGS

Further objects and advantages of the disclosure will become apparent from the following description and from the accompanying drawings, wherein:

FIGS. 9a and 9b are side perspective and top plan views of a mechanism of the first embodiment of the present disclosure, for limiting angular displacement.

FIGS. 12-14 are additional views of alternative mechanisms of the first embodiment of the present disclosure.

FIGS. 22-27 are further perspective views of the further embodiments of the present disclosure.

DETAILED DESCRIPTION OF THE PREFERRED EMBODIMENTS

Figure 1:
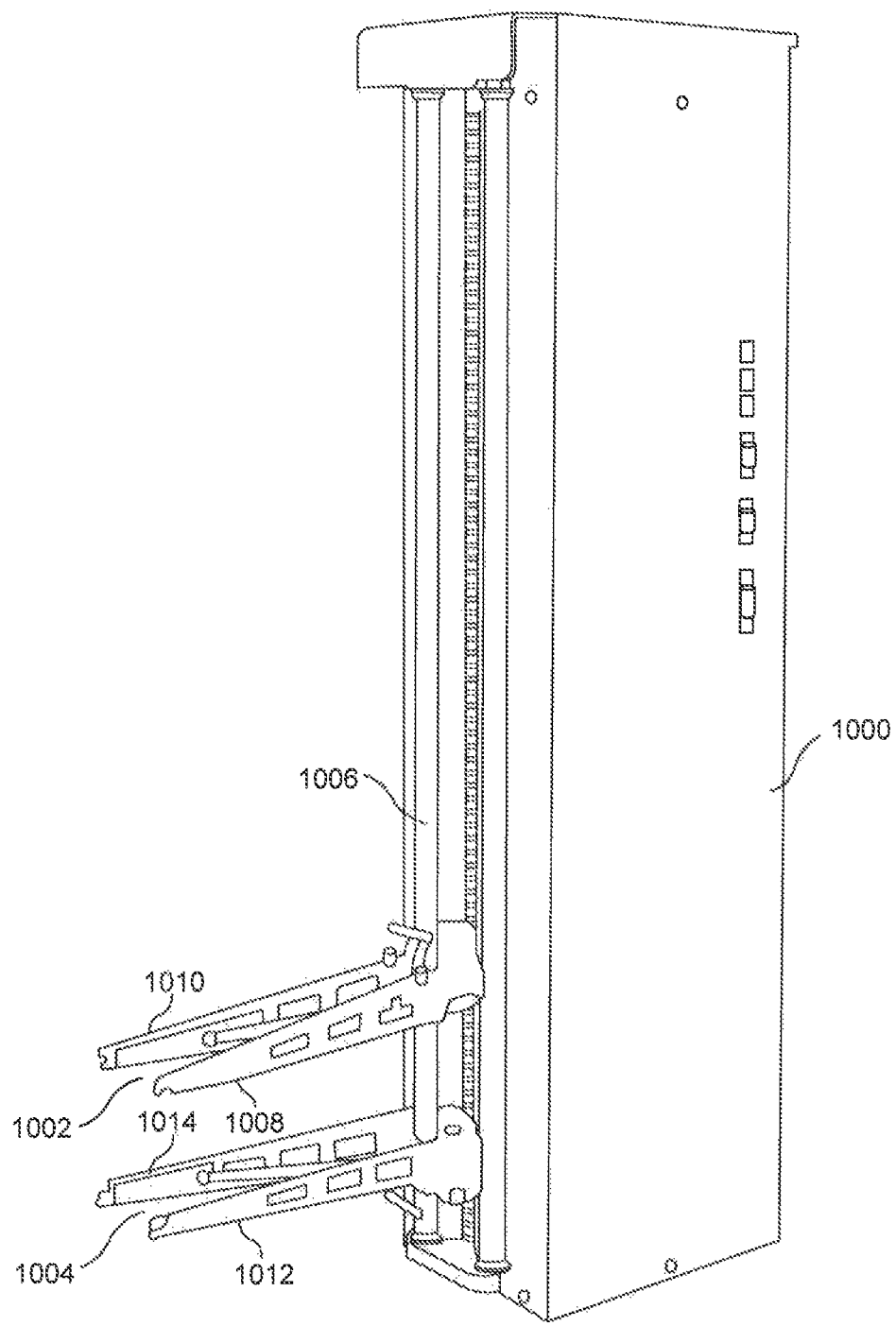
FIGS. 1-4 are illustrations of the prior art.

Referring now to the drawings in detail wherein like numerals indicate like elements throughout the several views, one sees that FIG. 1, while prior art, illustrates the general structure of an extensometer 1000. The extensometer 1000 includes an upper arm assembly 1002 and a lower arm assembly 1004 which are vertically aligned with each other along a vertical track 1006. Upper arm assembly 1002 includes two horizontally opposed contacting arms 1008, 1010 while lower arm assembly 1004 includes two horizontally opposed contacting arms 1012, 1014. The horizontally opposed contacting arms are pivotably articulated to grip respective ends of a specimen (not shown). Typically, then the upper and lower arm assembly track the movement of engaged points on the sample thereby measuring strain in response to grips (not shown) which impart a stress on the sample. The resulting strain on the sample, in response to the stress, is measured and plotted in order to determine the characteristics of the sample. However, the device of FIG. 1 does not use a linear encoder to measure the displacement of the arms.

Figure 2:
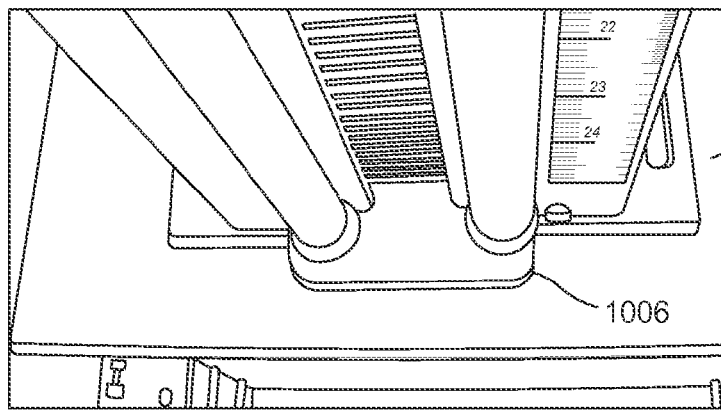
Figure 3:
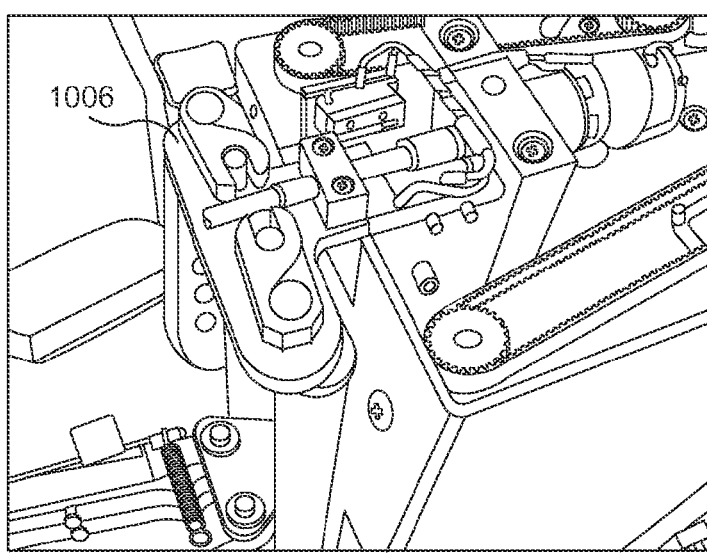
Figure 4:
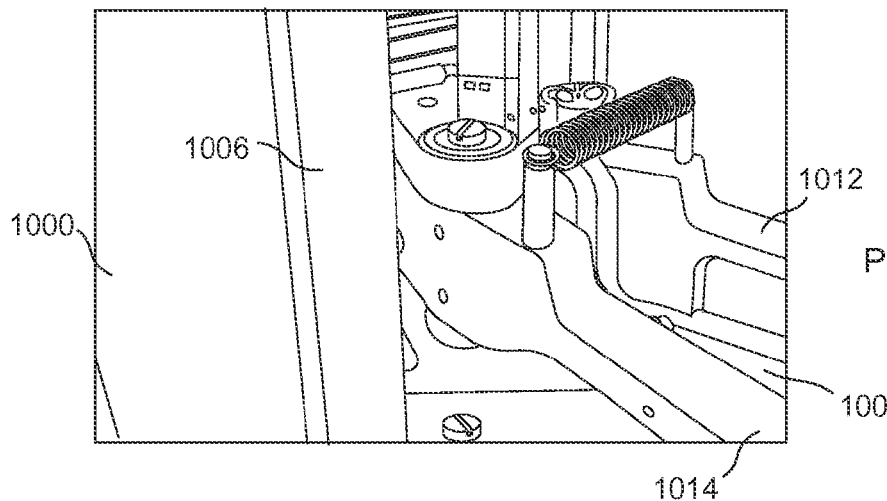

FIGS. 2-4 show the details of the arm assemblies 1002, 1004 and the vertical track 1006 of the prior art embodiment of FIG. 1.

Figure 5:
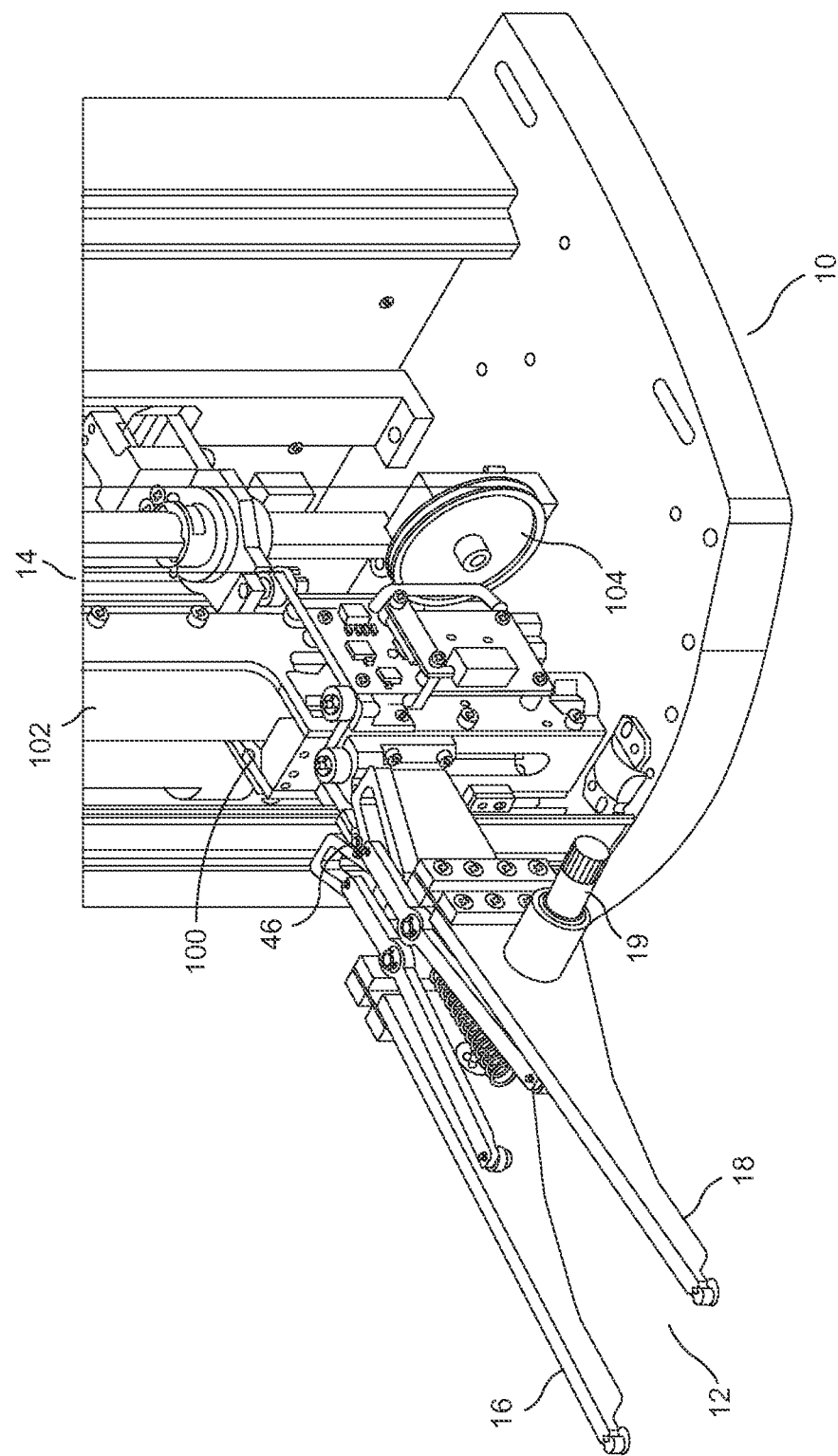
FIG. 5 is perspective view of the rotating bar mechanism on the lower arm of a first embodiment of the present disclosure.
Figure 6:
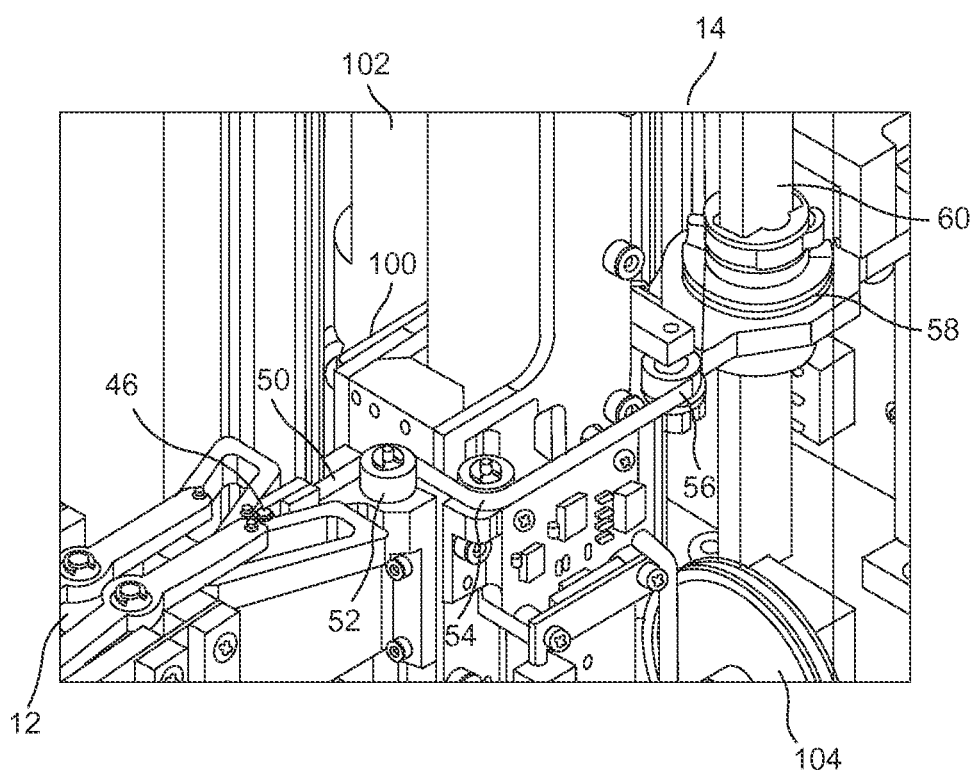
FIG. 6 is a perspective view of the arm actuation mechanism of a first embodiment of the present disclosure.
Figure 7:
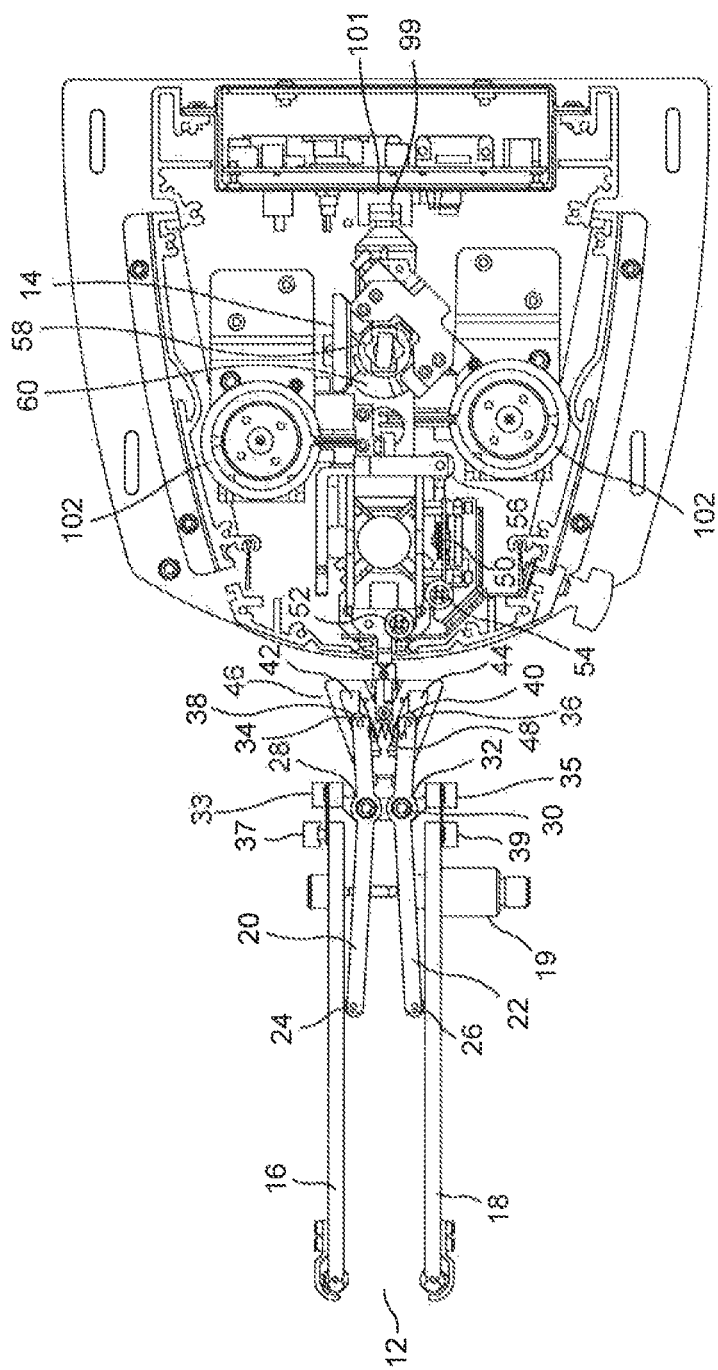
FIG. 7 is a top cross-sectional view of the arm actuation mechanism of the first embodiment of the present disclosure.

FIGS. 5-7 are perspective views the lower arm mechanism 12 and associated rotating bar mechanism 14 of an embodiment of the extensometer 10 of the present disclosure. Lower arm mechanism 12 is mounted on a carriage 100 which rides on vertical tracks 102 in response to pulley mechanism 104. Lower arm mechanism 12 further includes first lower contacting arm 16 and second lower contacting arm 18 which can be urged together in a gripping configuration by contact force adjustment assembly 19, which may be manually operated. As best shown in FIG. 7, first and second lever arms 20, 22 have respective first and second distal ends 24, 26 pivotably attached to the central interior portions of first and second lower contacting arms 16, 18. First and second lower lever arms 20, 22 further include respective first and second central pivot points 28, 30, pivotably mounted on cross-support member 32. First and second ends 33, 35 of cross-support member 32 provide a resilient flexible mount for the proximal ends 37, 39 of respective first and second lower contacting arms 16, 18. First and second lower lever arms 20, 22 further include first and second proximal ends 34, 36 which include respective first and second boss roller elements 38, 40. First and second boss roller elements 38, 40 are captured or engaged so as to travel within respective first and second inclined guide slots 42, 44 formed in a V-type configuration within wedge 46. Wedge 46 is biased by compression spring 48, mounted between first and second proximal ends 34, 36 of respective first and second lower lever arms, which urges first and second proximal ends 34, 36 apart, thereby urging wedge 46 in the left-hand direction of the orientation of the illustration in FIG. 7. When compression spring 48 urges the wedge 46 to a more left-hand position than shown in FIG. 7, the first and second roller elements 38, 40 are further separated from each other by the inclined configuration of guide slots 42, 44 thereby urging the first and second lever arms 20, 22 together thereby urging the first and second lower contacting arms 16, 18 together.

Wedge 46 is further attached to metal belt 50 (which may be implemented as a thin stainless steel shim), which is guided by rollers 52, 54, 56 and wrapped around spool 58 which is mounted on rotating bar 60. Rotating bar 60 goes through the arm assemblies inside of the extensometer. When bar 60 rotates, it winds the metal belt 50 around spool 58, thereby pulling wedge 46 to the right-most position in FIG. 7 (acting against the force of compression spring 48), thereby urging the first and second roller elements 38, 40 toward each other and pivoting the first and second lower contacting arms 16, 18 to an open position. This operation is done with no direct cam action on the part of rotating bar 60, but rather by the motion of the metal belt 50. As the bar 60 rotates clockwise, the spool 58 coils up the metal belt 50 and it in turn goes around the main structure of the extensometer 10 by means of rollers 52, 54, 56 until it pulls on wedge 46 and causes the motions as described above. By way of compression spring 48 urging first and second proximal ends 34, 36 apart, the extensometer 10 works in the opposite way and returns to its closed position when the motor rotates bar 60 counter-clockwise. A single rotating bar 60 is provided for the extensometer 10, with a separate spool 58 provided on bar 60 for each of the lower and upper arm assemblies 12, 13. In this manner, the contacting arms of the lower and upper arm assemblies 12, 13 typically operate in unison.

FIG. 7 further illustrates how the first embodiment of the present disclosure prevents contact with the rotating bar 60 during arm carriage motion. In an encoder-based extensometer architecture, having a rotating bar actuate the arms to open and close creates a substantial obstacle in that the bar 60 must stop making contact after opening and after closing. The requirement comes as a result of the added friction on the arm assemblies due to the bar 60 making contact with the rolling assemblies to which the arms are attached. An objective in a contacting extensometer may be the goal of making the complete arm sub-assembly carriage have reduced or eliminated running forces due to weight which impinge upon critical elements (i.e., sometimes referred to by those skilled in the art as being "weightless"). The arm carriages typically would have to be precisely counter-balanced and significant effort must be invested in keeping rolling surfaces as frictionless as possible. This is typically difficult to accomplish in order to maintain accuracy that having the bar making contact during testing is typically not practically feasible. The added friction would deflect the contacting arms and the forces required to move the carriages would typically both be expected to produce large errors.

As a result, a mechanism is provided to back-drive the bar 60 from its open or closed angular position to a free position where there is no contact with the spool 58, which is mounted on spool bearing 85 on base plate 87. As shown on FIG. 8, a vertically camming bearing profile 66 is provided along the outer edge of spool 58, upon which small bearing 68 rides. The bearing 68 is attached to a spring-loaded flexure 70 (which may be provided by a torsion spring assembly) that always ensures downward preloading. The vertically camming bearing profile 66 upon which the bearing 68 rides has a pocket 72 to capture or to detent engage bearing 68 in the lower closed position, and another in the upper open position (not shown). The upper open position may also be implemented with a stop pin rather than a pocket, because spring-loaded flexure 70 forces in the arms to bias the mechanism towards this position. The force of the spring-loaded flexure 70 also typically requires a precise shaping of vertically camming bearing profile 66, as opposed to a horizontal surface which may cause the first and second contacting arms 16, 18 to snap closed, which is unacceptable as the sharp contact points in the arms may damage specimens. This mechanism is intended to eliminate bar contact during carriage travel. Additionally, the rear of carriage 100 includes a bearing 99 for riding in track 101.

In order to improve the performance of the vertically camming bearing profile, the motor typically must be controlled in such a way as to know when to stop turning and reverse direction, and when to stop the reverse motion and position itself in the free range. In other words, angular displacement must be limited so that the range of rotation of the rotating bar 60 is controlled. As shown on FIG. 9a, in order to minimize or reduce expensive motion control, at the top of the bar 60 there is a flat wedge 76 with radial edges 78, 80 (i.e., pie-shaped or partially circular) that cross the path of a fixed optical switch 81 as it rotates with the bar 60. The radial edges 78, 80 break the optical signal and trigger the motor to stop or reverse, in effect acting as a rotary encoder. This not only typically rotationally positions the bar 60 to be in an accurate and repeatable stop in the contact-free zone, but also stops the motor reverse direction at a precise point without over-torqueing the carriage assemblies. FIG. 9b shows a top view of the mechanism with the bar 60 in the middle of the contact-free position.

Figure 10A:
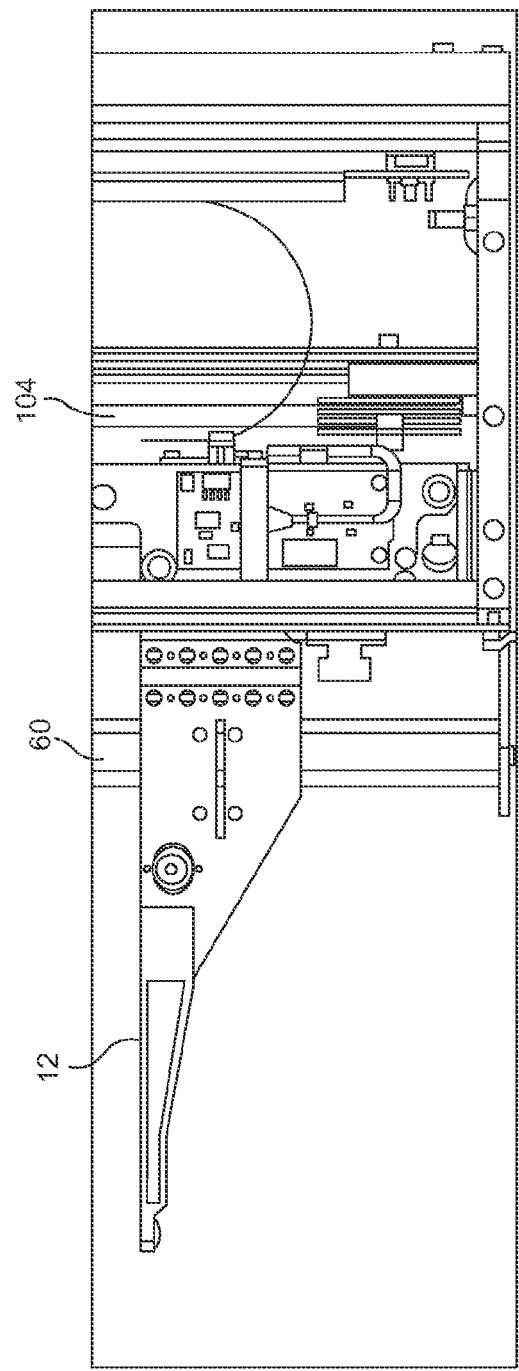
FIGS. 10a and 10b are side plan views of a mechanism the first embodiment of the present disclosure for eliminating bar contact during carriage travel.
Figure 10B:
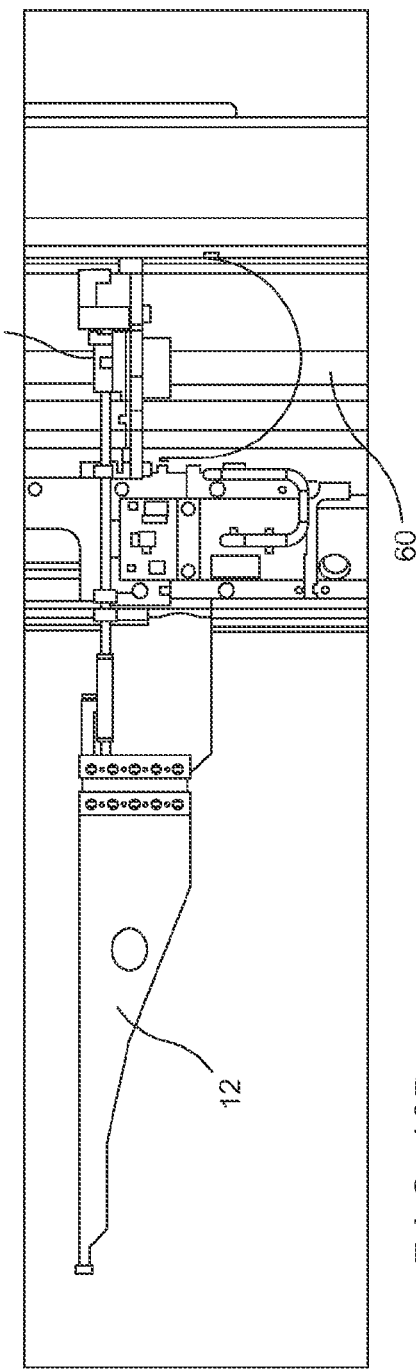

FIGS. 10a and 10b illustrate the advantages of moving the bar inside, to the back of the extensometer 10. An objective of an extensometer 10 may be to reach over a set of grips or other similar devices holding a specimen. As such, the amount of reach of the contacting arms is absolutely necessary for the instrument to be compatible with larger grips. There are, however, practical limitations as to how far arms can reach. The distance from the contacting point of the arms to the point where the measurement is made inside is incredibly sensitive to minute deflections, bearing surface imperfections, and increases in drag. Consequently, maximizing the amount of that distance devoted to actual test reach is crucial. This, in effect, means that any distance forward of the measurement encoder not free to clear grips is lost reach. Placing the mechanism at the back means zero reach lost to the actuation mechanism. For reference, note the difference in reach from an earlier experimental prototype using an external bar on FIG. 10a versus the internal bar on FIG. 10b. In an embodiment of the disclosure illustrated in FIG. 10b, over 65 millimeters of additional reach resulted from the internal packaging of the bar at the rear of the extensometer, as compared to the extensometer of FIG. 10a.

Figure 11:
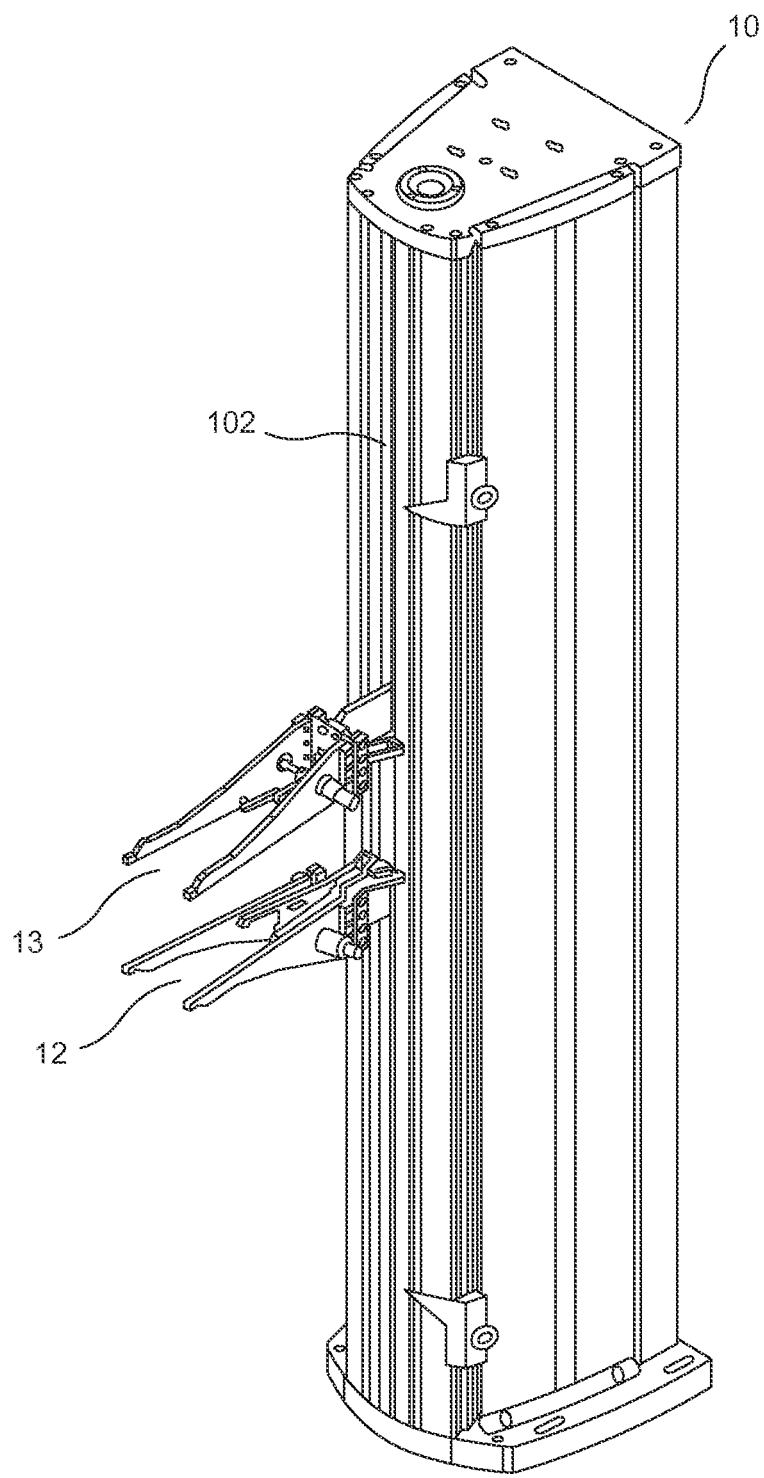
FIG. 11 is a perspective view of the first embodiment of the present disclosure.
Figure 12:
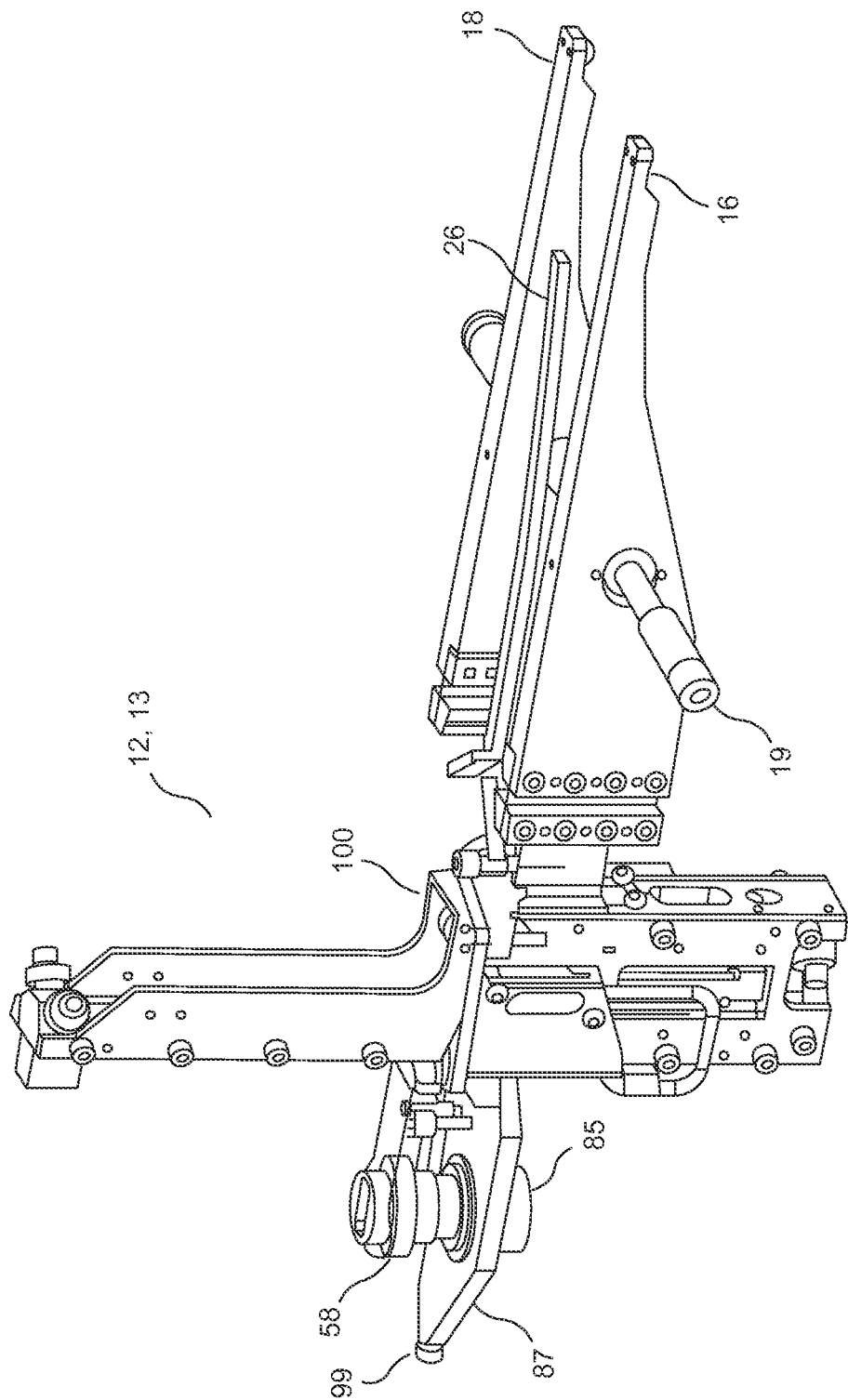
Figure 14:
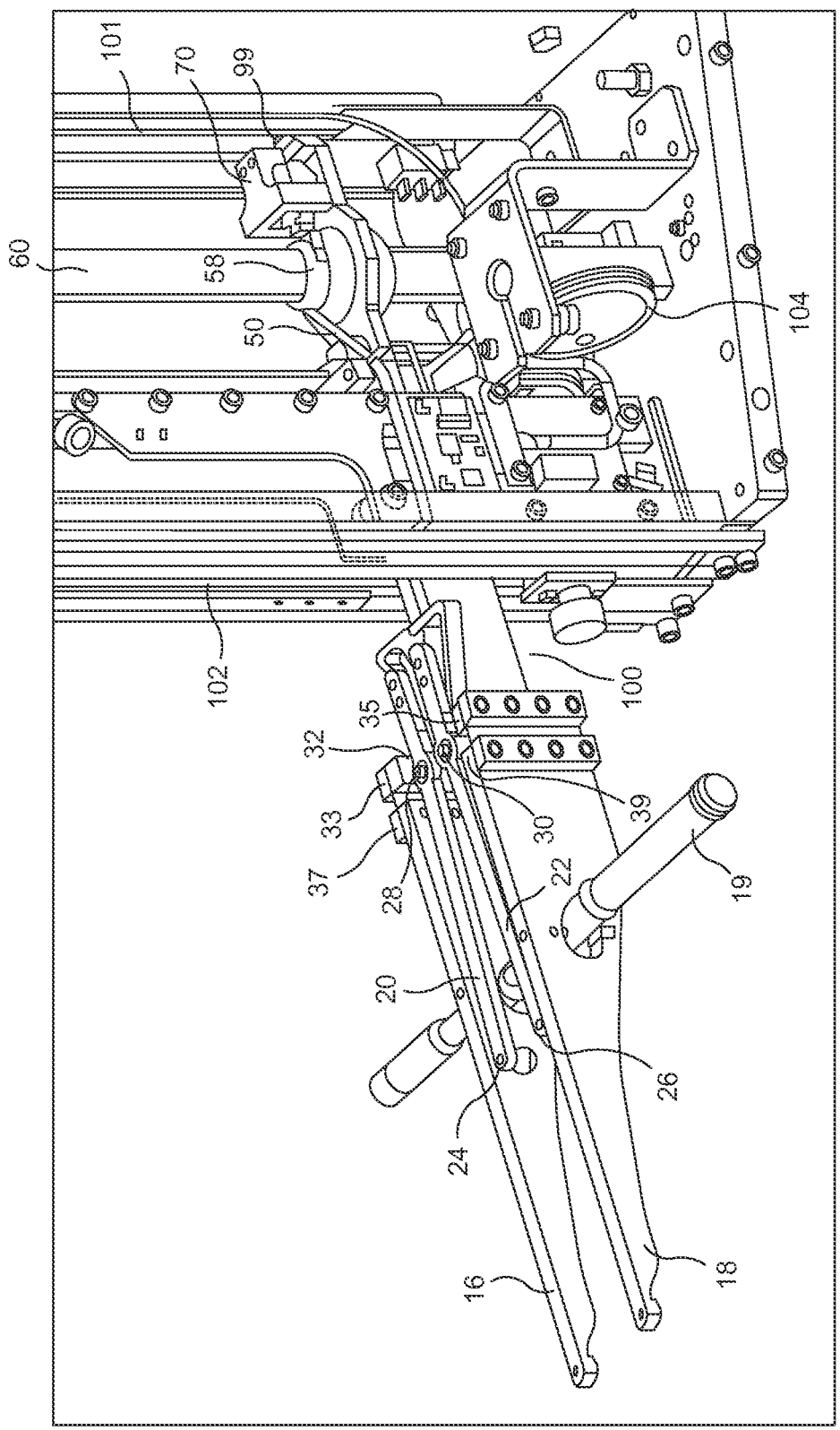

FIG. 11 is a perspective view of an embodiment of extensometer 10, including lower arm mechanism 12 and upper arm mechanism 13 (with substantially the same structure as lower arm mechanism 12, but typically inverted) while FIGS. 12-14 include further alternative variations of the disclosure.

Figure 8:
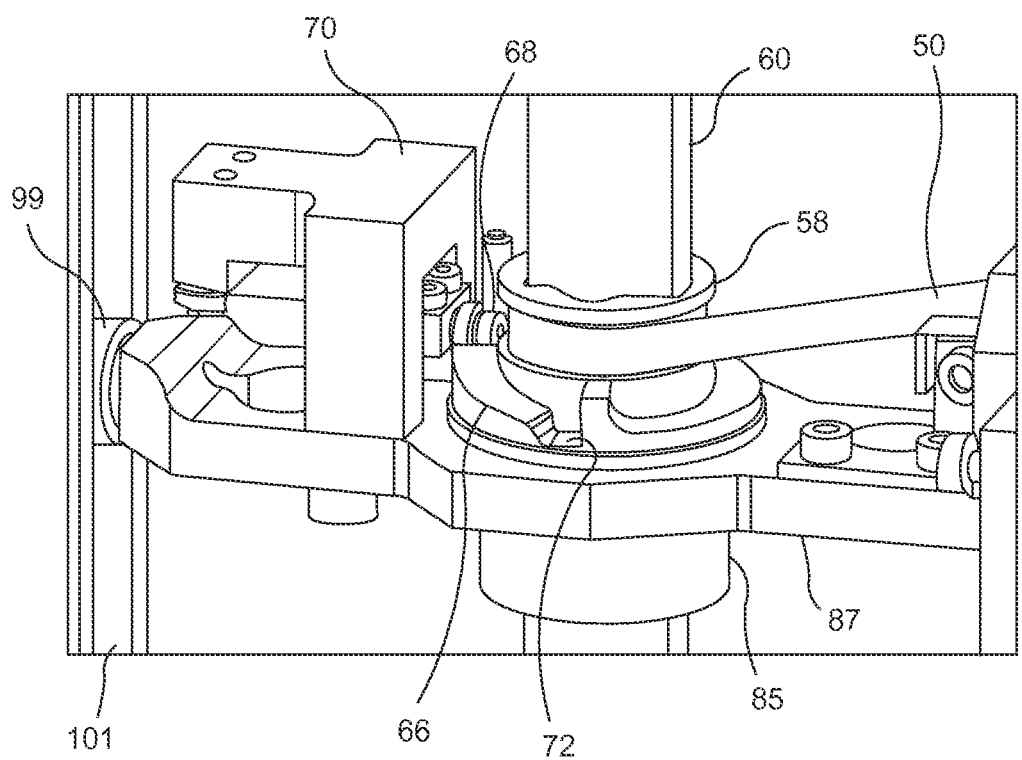
FIG. 8 is a perspective view of a portion of the mechanism of the first embodiment of the present disclosure.
Figure 15:
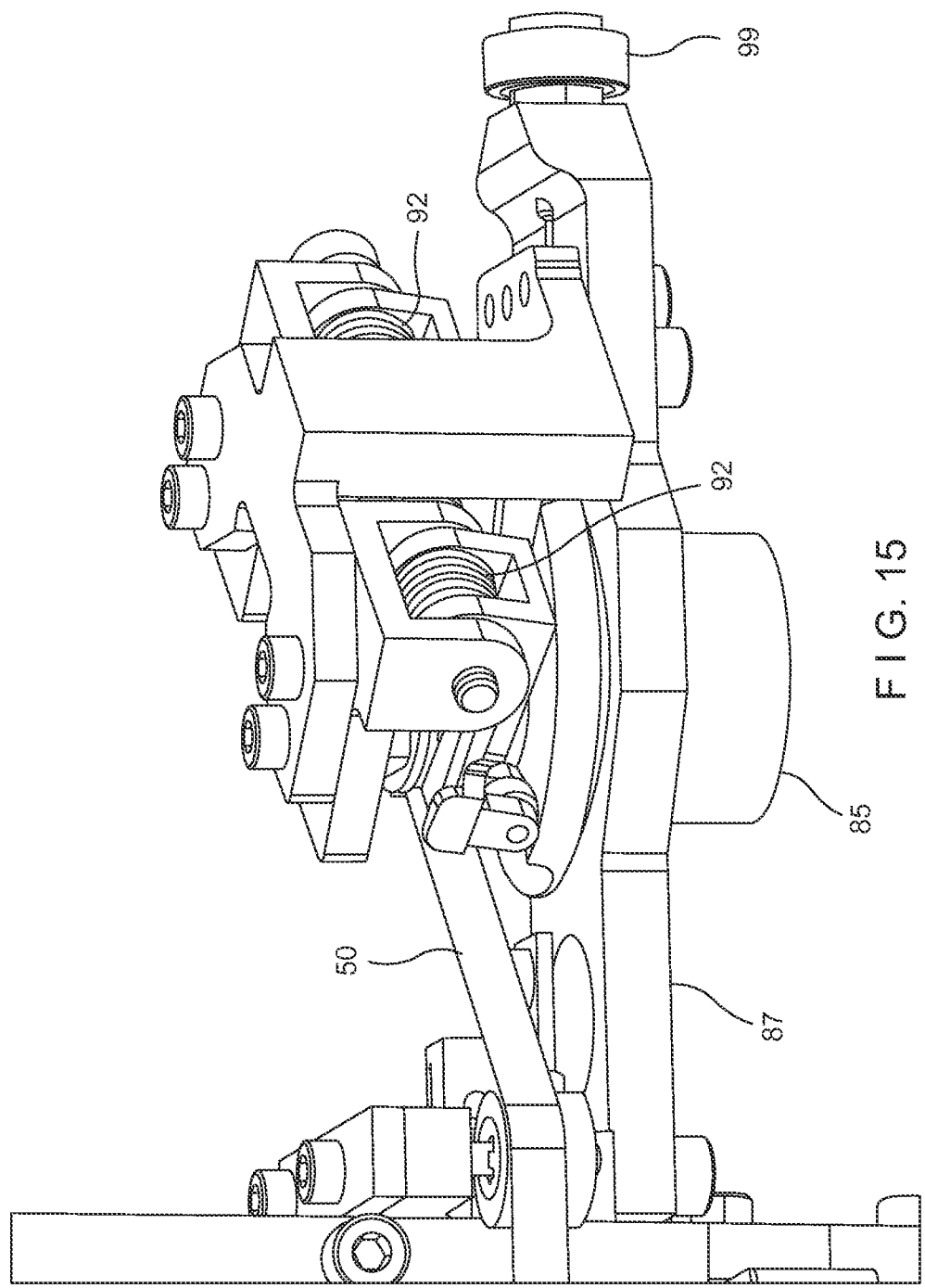
FIGS. 15 and 16 are perspective views of a mechanism that holds the angular position of the rotating spool.
Figure 16:
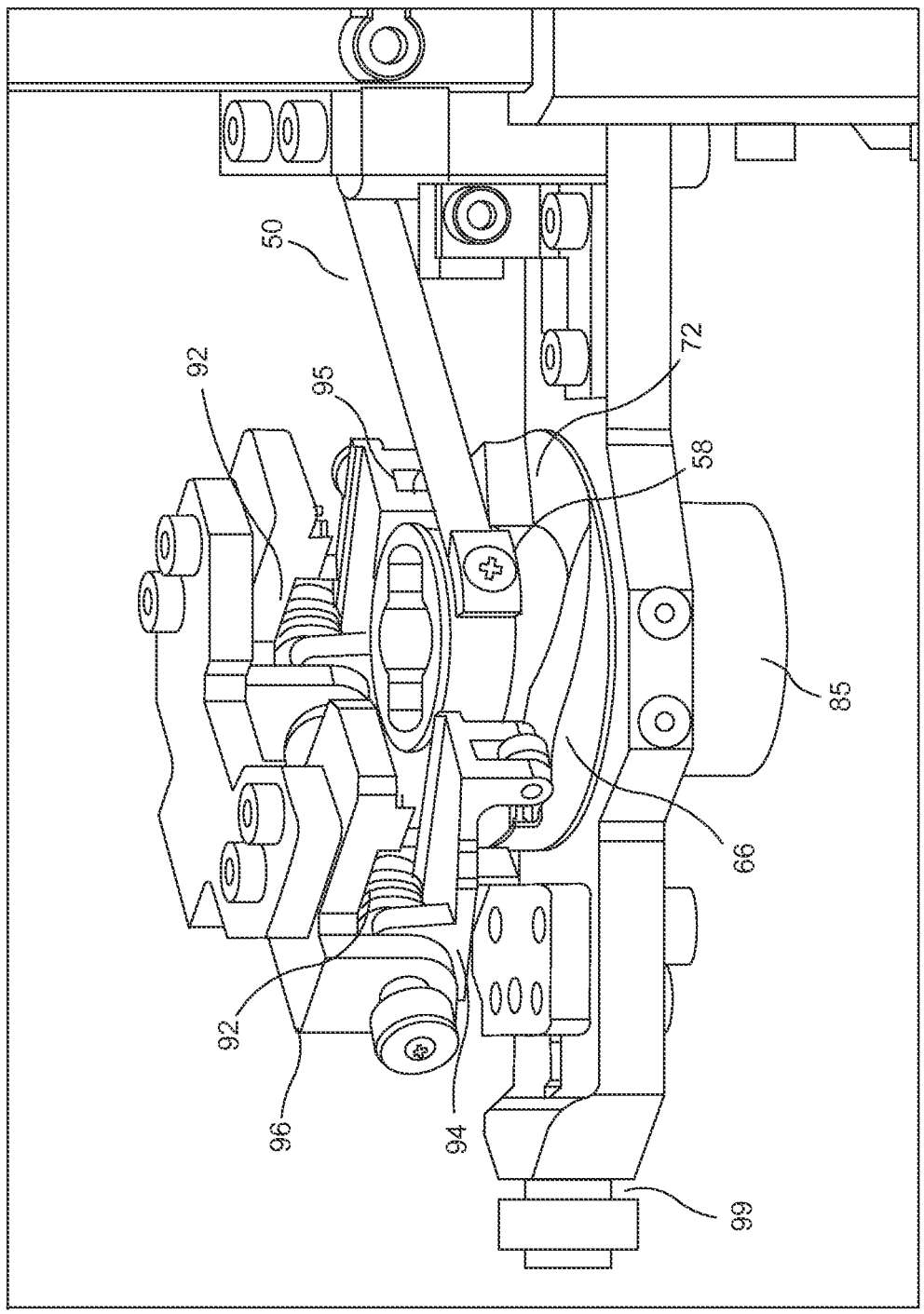

FIGS. 15 and 16 pertain to a mechanism of the spool bearing 85, mounted on base plate 87 of carriage 100, that holds the angular position of the rotating spool 58 to prevent contact with the bar 60. This design has a similar cam structure 66 as illustrated in FIG. 8 and is based on the use of torsion springs 92 to pivotably mount plate 94 onto plate 96, wherein rollers 95 are mounted on plate 94 are biased against cam structure 66 by the force of torsion springs 92, rather than the spring-loaded flexure 70 of FIG. 8, to provide substantially improved life. The ramp and pocket geometry is implemented by cam structure 66 and pocket 72, wherein pocket 72 can capture one of rollers 95.

Figure 17:
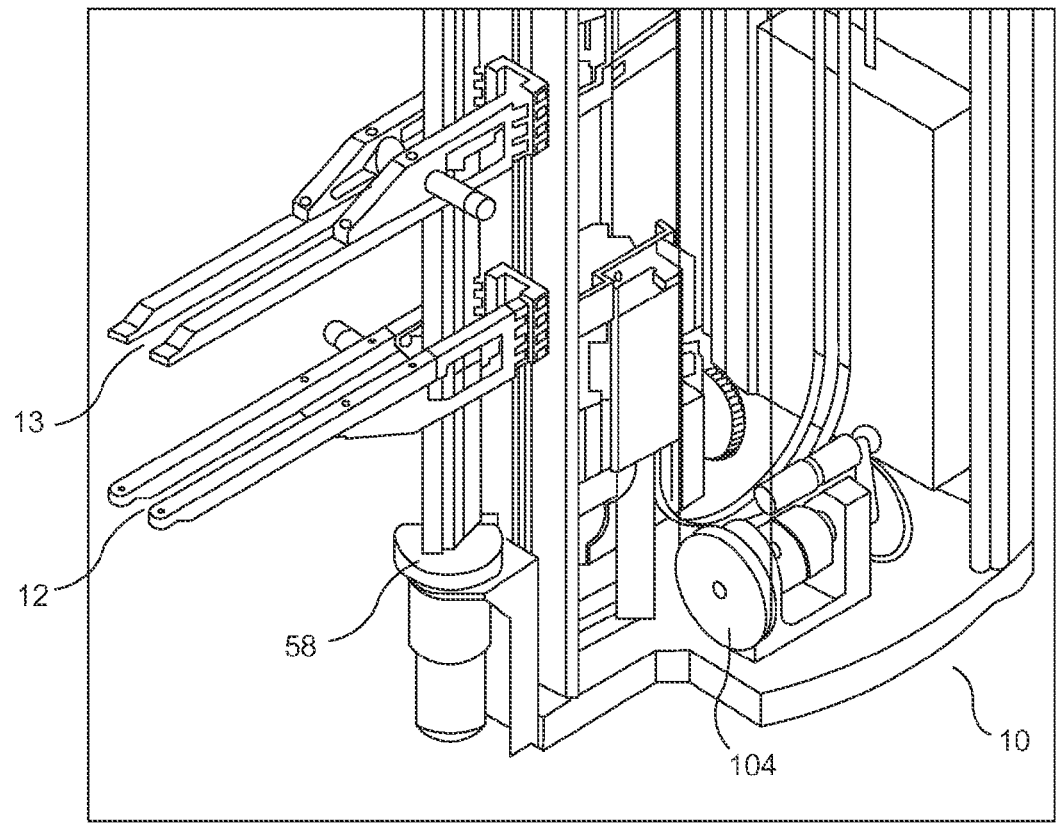
FIG. 17 is a perspective view of the opening bar system of a second embodiment of the present disclosure.
Figure 18B:
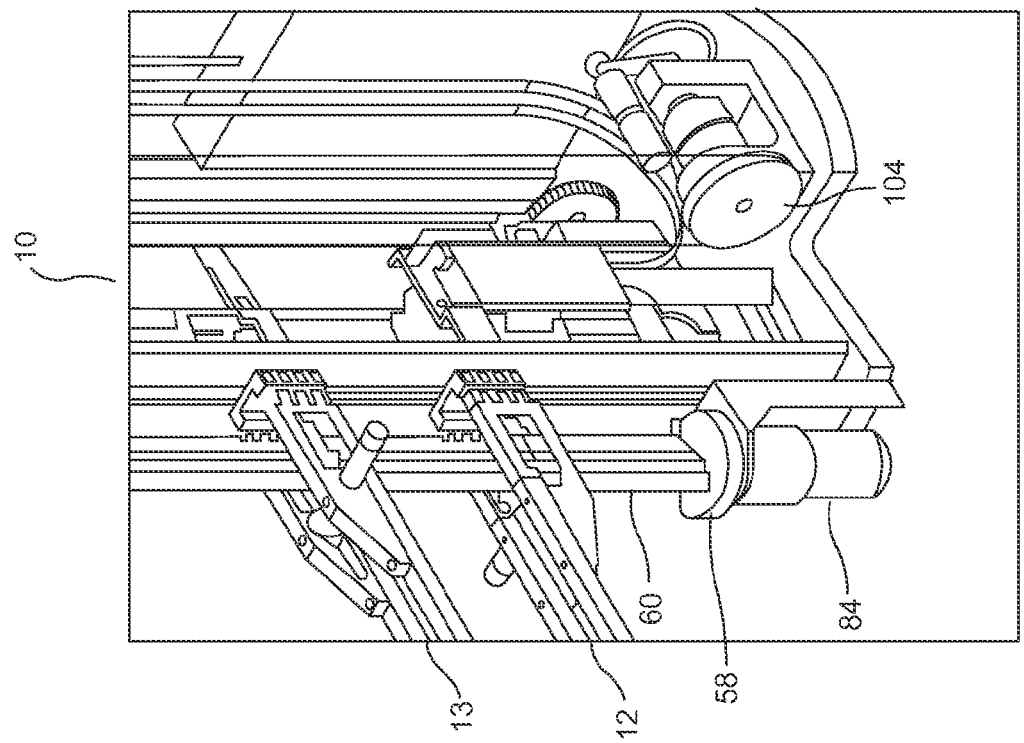
FIGS. 18a and 18b are top and bottom views, respectively, of the rotating bar pivot points of a second embodiment of the present disclosure.
Figure 18A:
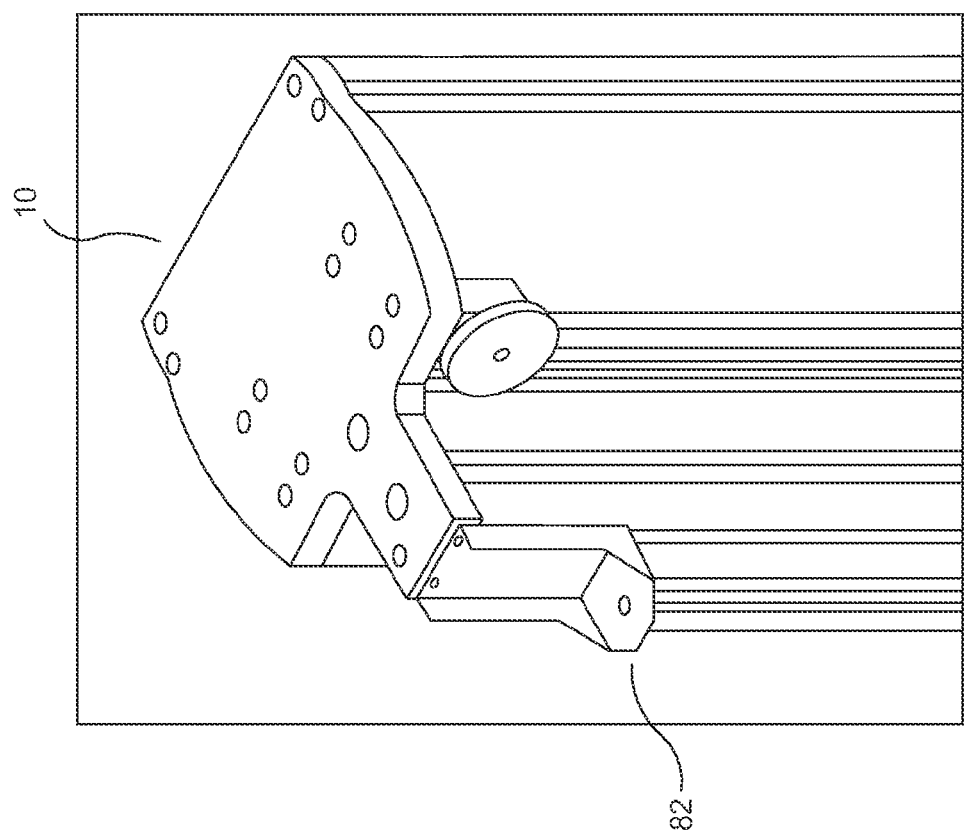
Figure 19:
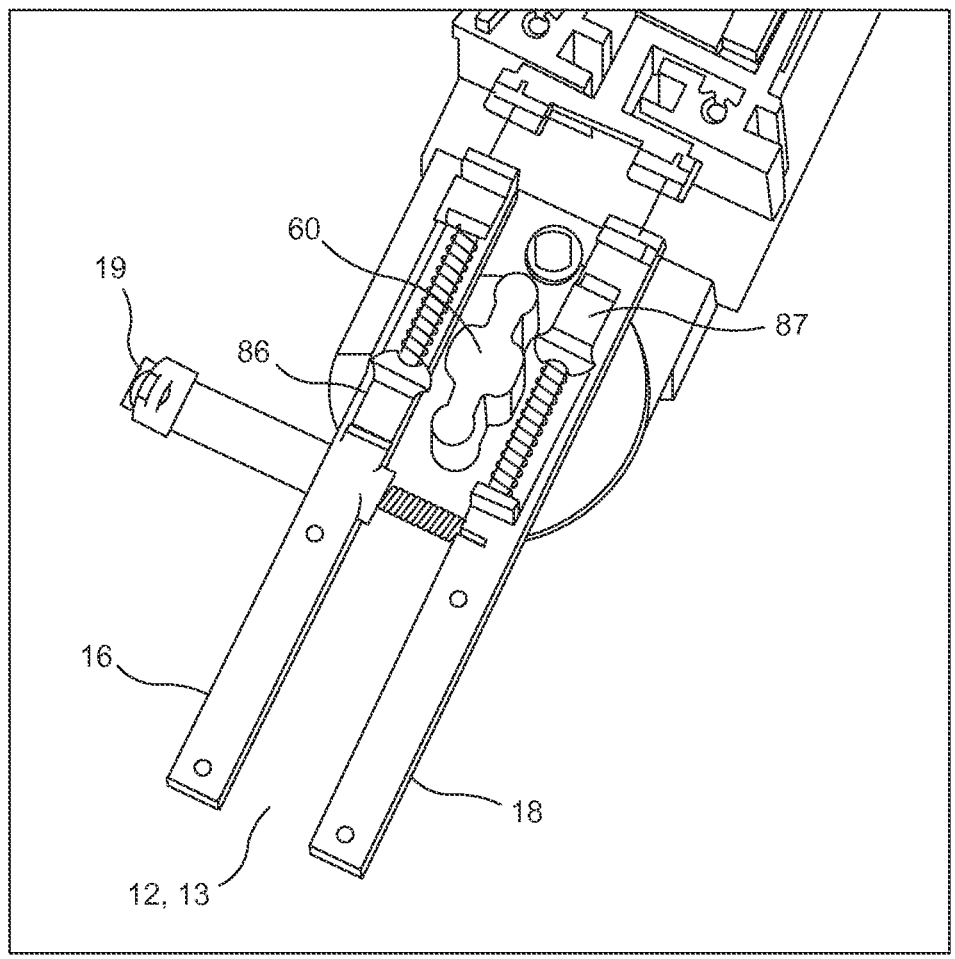
FIG. 19 is a perspective view of the arms in the closed position in the second embodiment of the present disclosure.
Figure 20:
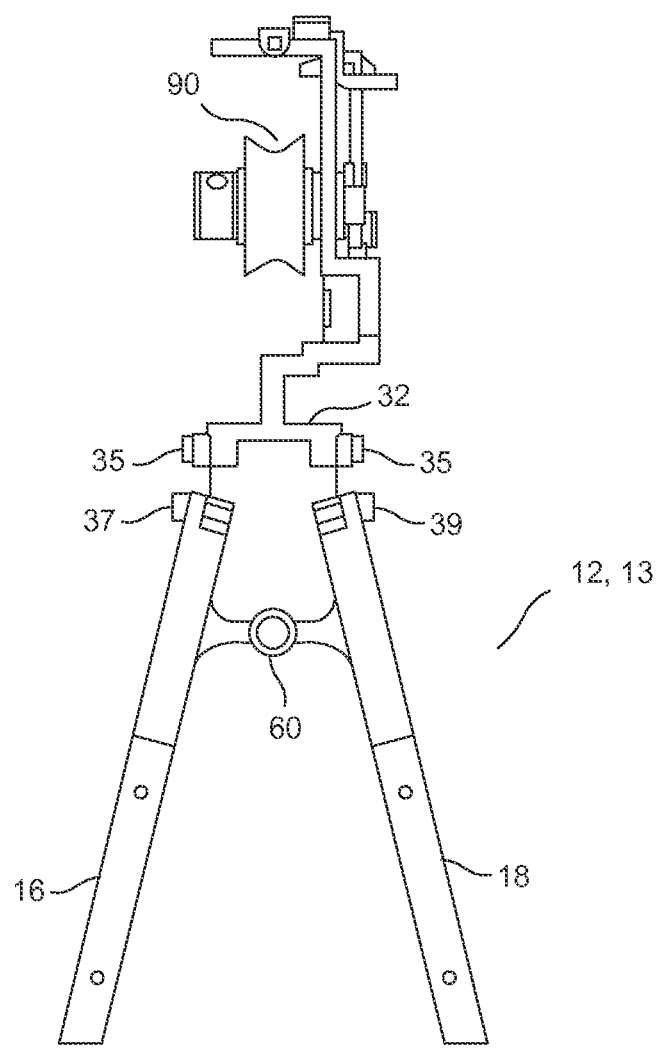
FIG. 20 is a perspective view of the arms in the open position in response to the rotation of the bar in the second embodiment of the present disclosure.
Figure 21:
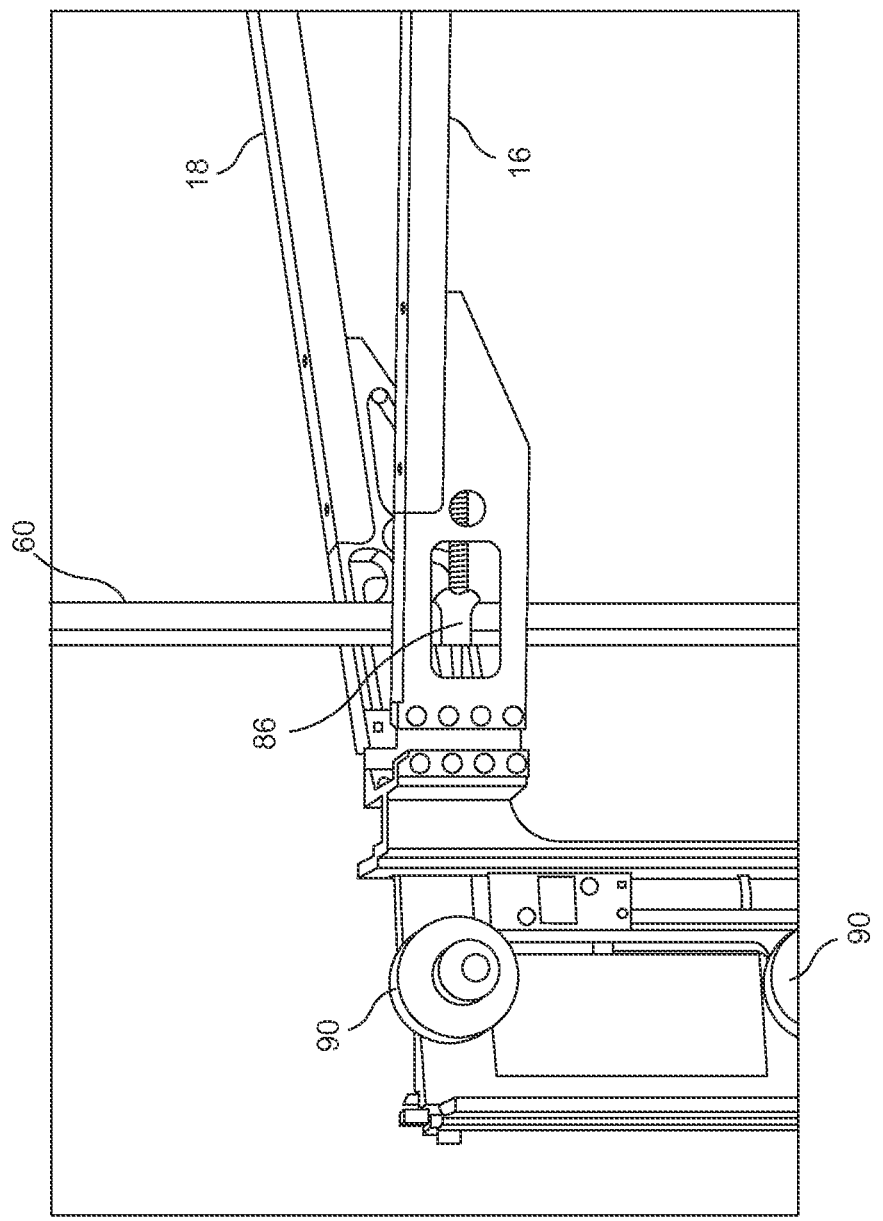
FIG. 21 is a perspective view of a sliding roller in the second embodiment of the present disclosure.
Figure 23:
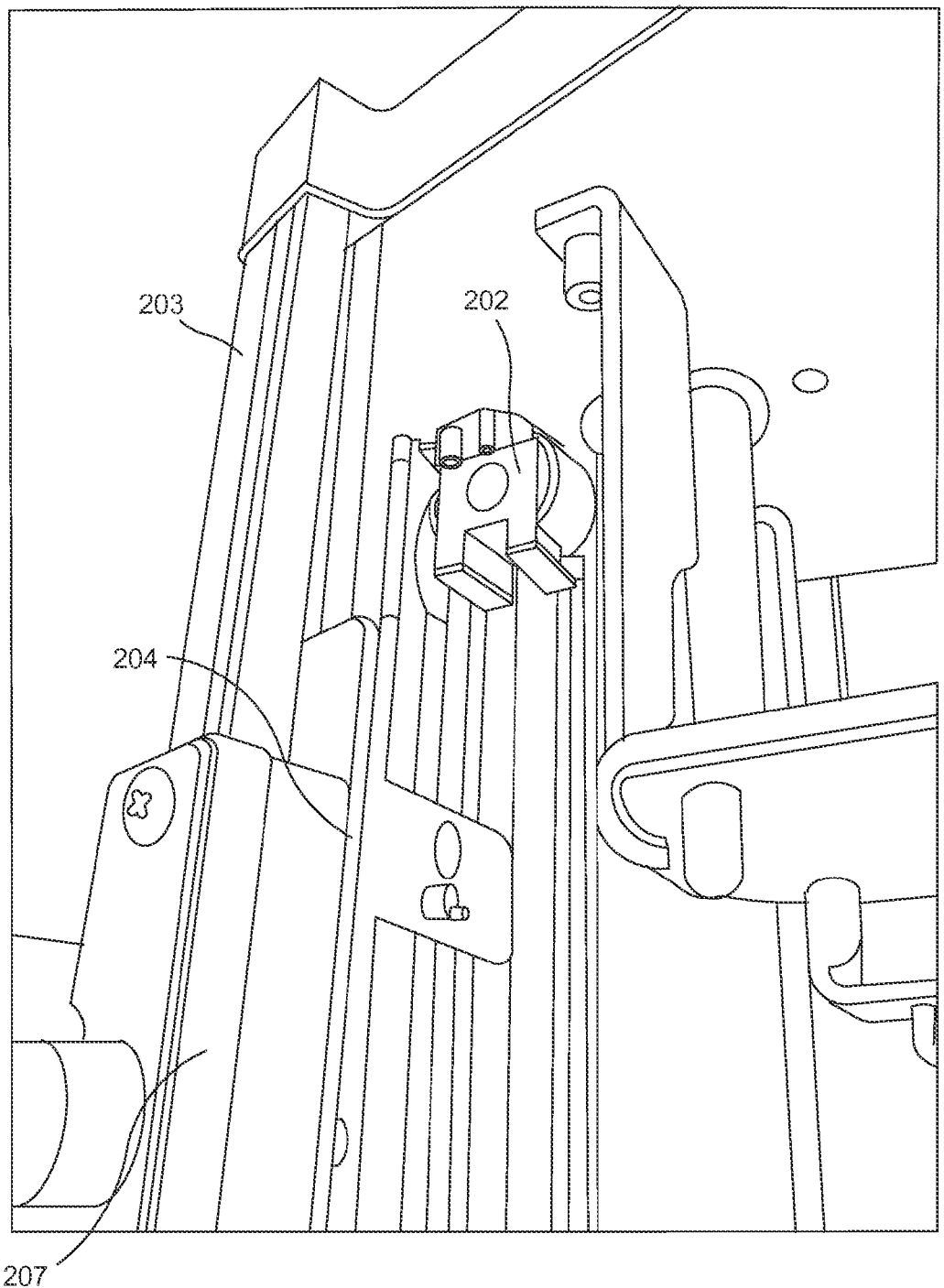

The second embodiment of the disclosure is illustrated in FIGS. 17-21. FIG. 17 is a perspective view of the opening bar system of the second embodiment of this disclosure. In this second embodiment, the rotating bar or opening bar 60 is supported on top and bottom by respective upper and lower pivots or bearings 82, 84 as shown in FIGS. 18a and 18b thereby allowing it to rotate along its length. The aspect ratio of the rotating bar 60 enables the device to be clear of the arms of lower and upper arm mechanisms 12, 13 in the closed arm position of FIG. 19. This clearance is typically important as it eliminates friction between the opening bar 60 and the arms 16, 18 of the lower and upper arm mechanisms 12, 13, thereby enabling the arms to follow the test sample with minimal drag. When the bar 60 is rotated so that its wider dimension is transverse between the arms 16, 18, the arms 16, 18 are forced open, the edges of the bar 60 engage with the spring-loaded sliding rollers 86, 87 (which are freely rotating and traverse a longitudinal portion of arms 16, 18) thereby reducing the friction between the opening bar 60 and the arms 16, 18. The arms 16, 18 are forced open by the rotated bar 60 as illustrated in FIGS. 20 and 21. The opening bar 60 can be motor driven or manually operated. The arms 16, 18 themselves contain sliding runners that are free to rotate. The vertical rollers 90 illustrated in FIG. 21 allow the lower and upper arm mechanisms 12, 13 to travel vertically while the opening bar is engaged. In summary, the rotating bar mechanism is used to open and close two sets of hinged mechanical arms on a long travel extensometer.

FIGS. 22-27 are further perspective views of the further embodiments of the present disclosure. These embodiments include a device to mitigate debris from entering the device by the use of a constant force spring acting as a roll-up shade-type configuration and an improved way to repeatably adjust the tension of the spring that controls the amount of force the contacting arms puts on the specimen.

Figure 24:
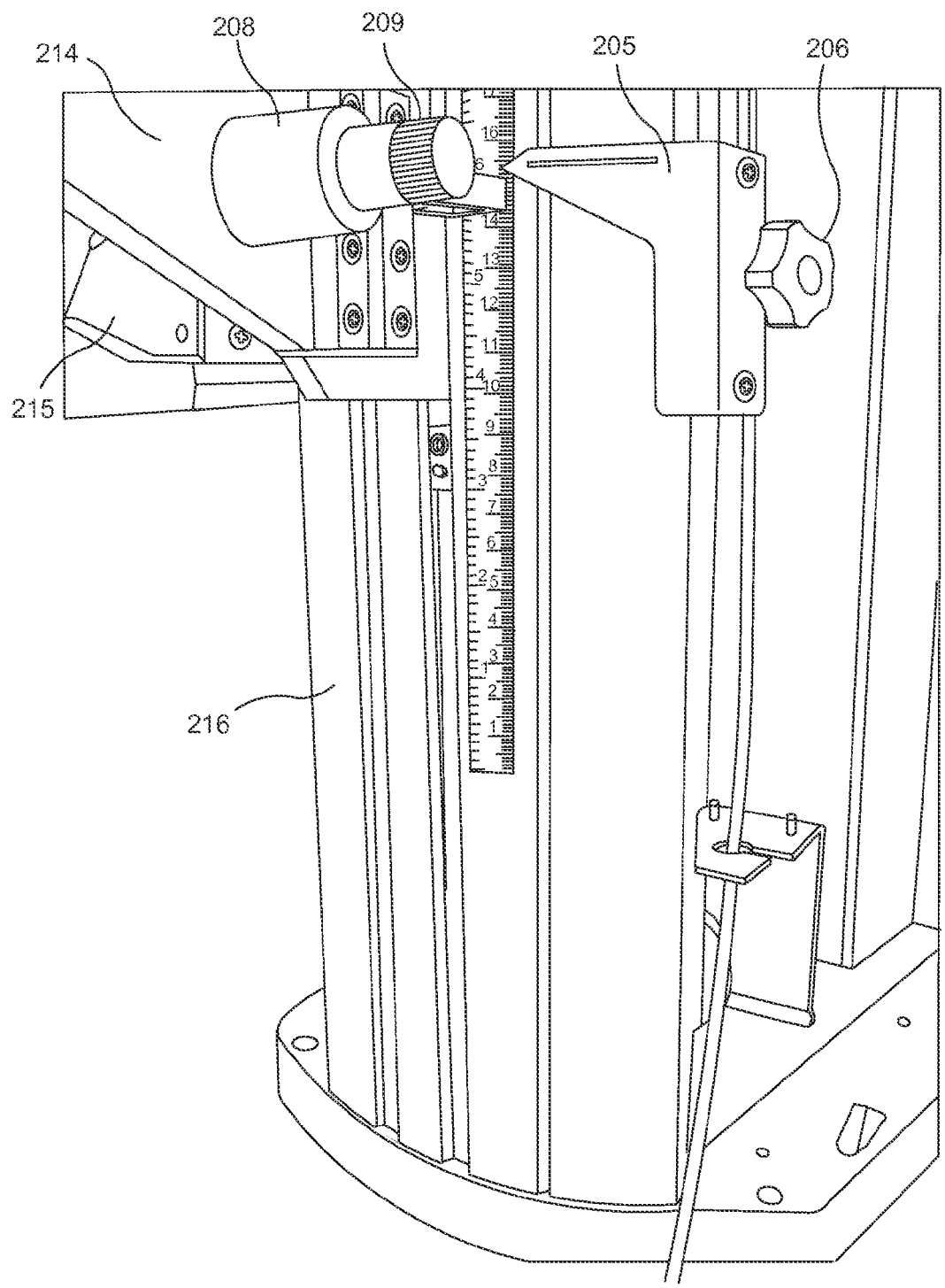
Figure 25:
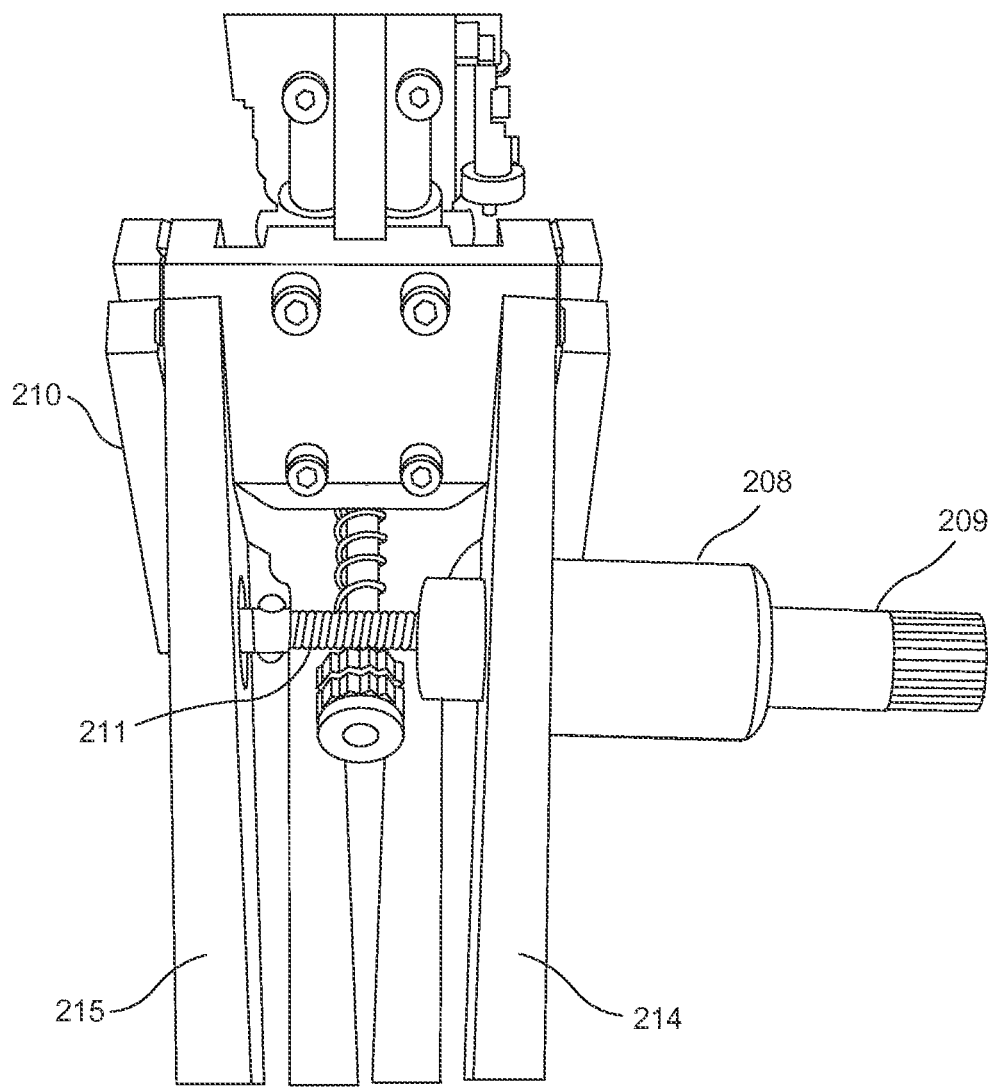
Figure 26:
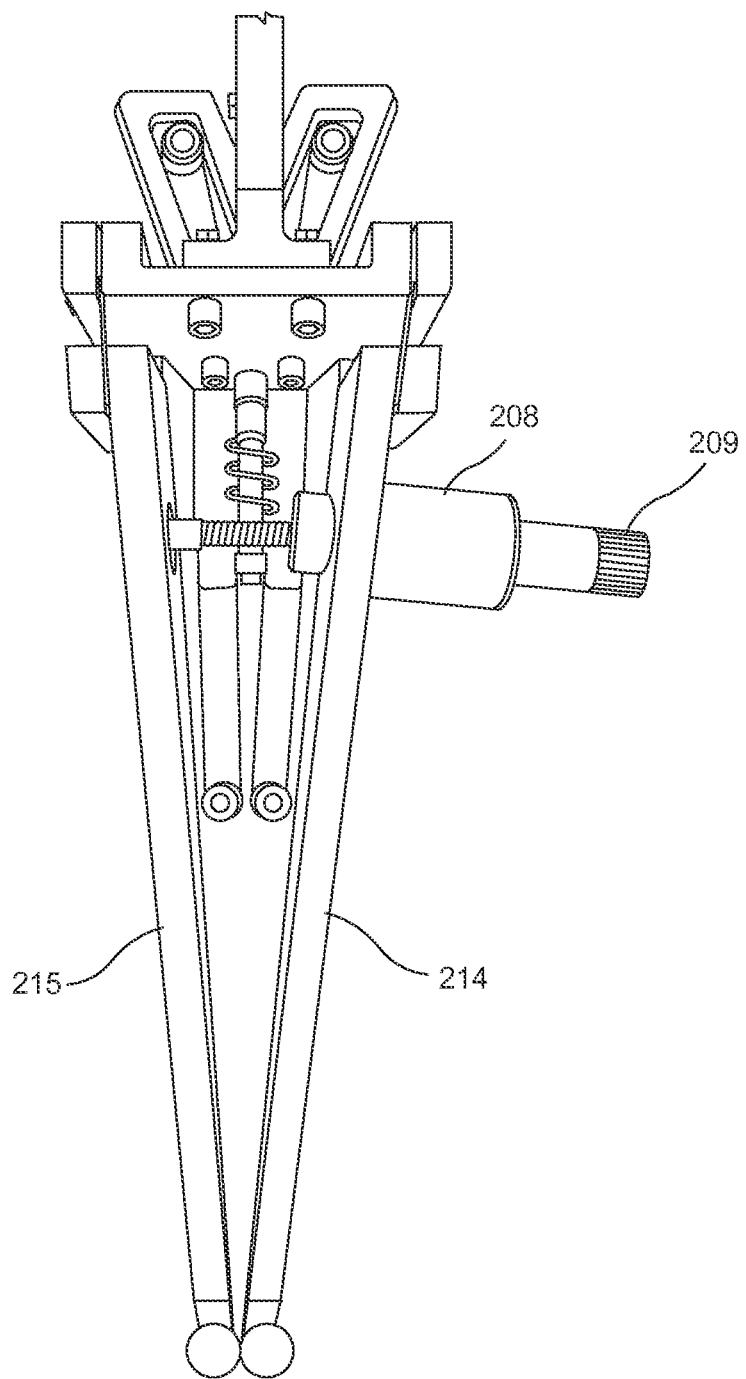
Figure 27:
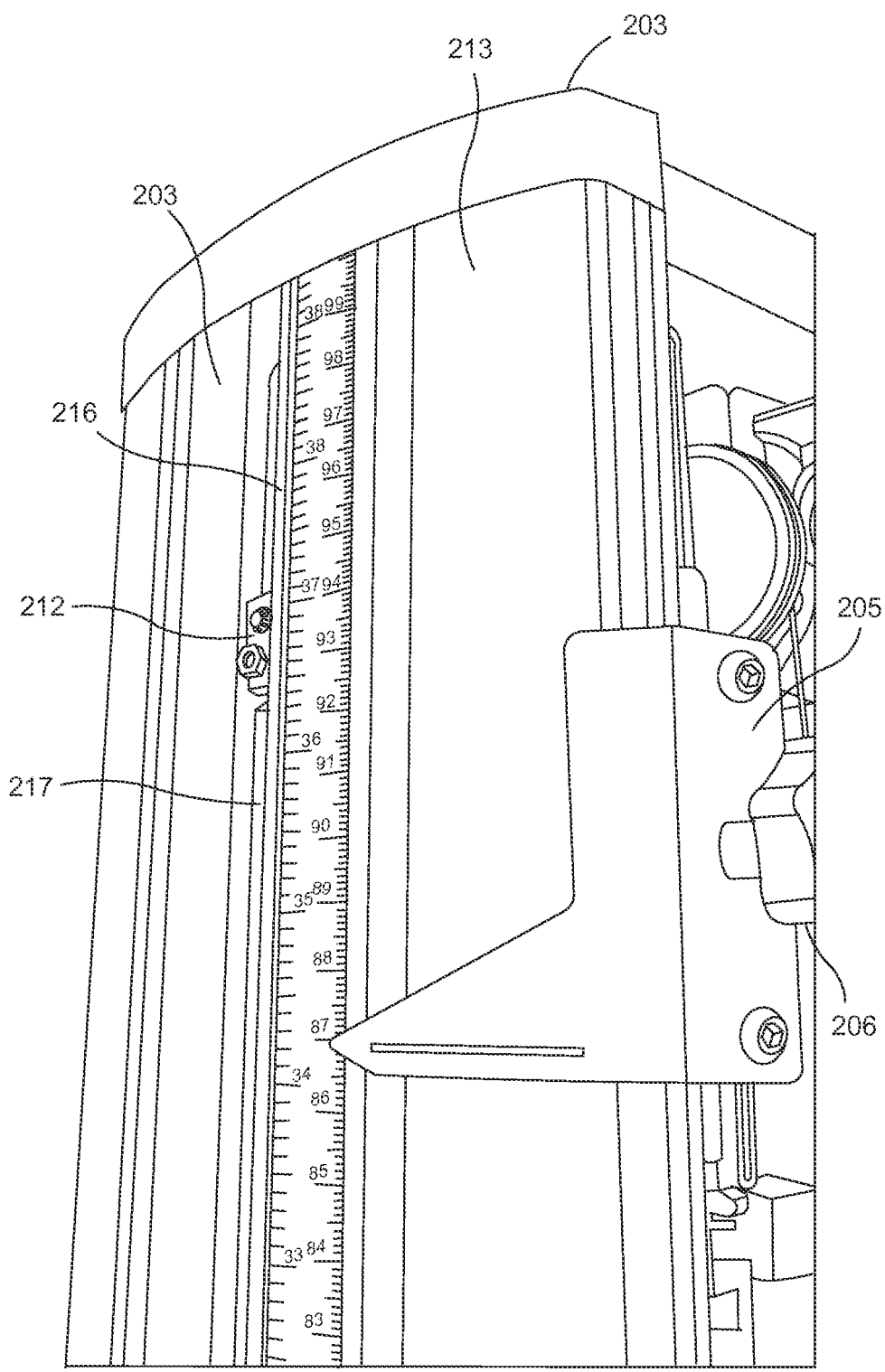

The tensioner assembly, shown on FIGS. 24-26, includes knob 209 with markings which controls the extension of spring 211, which draws arms 214, 215 together. One end of spring 211 is held captive to arm 215 by means of a swiveling anchor, thereby allowing the spring to rotate freely on that end. At the other end of spring 211, the spring is held captive to arm 214 by being attached to threaded knob 209. Knob 209 is threaded against a threaded sleeve 208 that is fixed on to arm 214. As knob 209 is rotated, it changes the length of extension spring 211, altering the force with which spring 211 pulls the contacting arms 214, 215 together. In addition, as knob 209 is rotated along the threads, more or less of knob 209 is exposed from beneath threaded sleeve 208. The amount of knob 209 exposed can be quantified by markings on knob 209. As a result, a user can rotate knob 209 to a desired contacting force setting and use the exposed markings on it as reference to achieve the same contacting force in future tests.

FIGS. 22-24 and 27 show the debris shield assemblies. There are two debris shield assemblies (upper and lower, mirrored) including a constant-force-spring 200 coiled around a spool assembly 202. Spring 200 is fed along channels on bilateral extrusions 203 and attached to a bracket 204 by means of a clamp 212. Bracket 204 is secured onto extrusion 203 using slide 207 on the opposite side. These two parts are clamped together with knob 206. Indicator plate 205 covers slide 207. The travel limit assemblies can slide vertically along features on extrusion 203 until the desired location. The user then tightens knob 206 and the vertical location becomes fixed. The extensometer design makes use of travel limits to protect the arms assemblies from damage by running into fixed objects in the test setup. The apparatus makes use of these travel limit assemblies to uncoil and recoil the constant force spring covering up gaps between extrusions 203 on positions the contacting arms will not use during a test. As a result, the open area of the extensometer is minimized and can thus mitigate the amount of debris from broken specimens and other environmental contaminants from finding their way into the extensometer. Element 216 shows areas covered by the debris shield assembly and element 217 shows exposed areas open to the inside of the extensometer. As the user sets the limits of travel, the apparatus automatically covers up unused areas with a low-cost design.

In conclusion, the instrument will benefit from the inherent protection the mechanism gets by being inside the instrument. Specimen breaks can be very violent, dusty, and can send sections of specimens as projectiles. Also, any noise produced by the mechanism is muffled by being inside. The look of the instrument becomes cleaner and sleeker. Finally, this mechanism is less expensive, as there is no need for external covers or cosmetic consideration.

The resulting apparatus typically achieves several advantages. If using an external rotating bar to actuate the arms, redesigned arms would be required to develop a longer-reach variant extensometer, an expensive and difficult technical task considered a sub-project on its own. With this disclosure, the arms typically do not change. Typically only the simple piece connecting the arms to the carriage needs to grow along with the length of the simple metal belt. This advantage is in addition to the aforementioned gain in reach by removing the mechanism itself. Together, this disclosure improves feasible arm reach while keeping development and part costs low.

Similarly, there is a growing need in the marketplace to use extensometers in high-temperature applications. By removing the actuating mechanism form the front of the instrument and being able to extend just one part with a thin with a thin cross section to gain additional reach, this product will readily be able to be configured for use in high-temperature chambers inside of which the arms must fully reside. The design can be easily adapted to only have high temperature-safe materials where required and the chamber opening can remain small.

Thus the several aforementioned objects and advantages are most effectively attained. Although preferred embodiments of the invention have been disclosed and described in detail herein, it should be understood that this invention is in no sense limited thereby and its scope is to be determined by that of the appended claims.

What is claimed is:

1. An extensometer including:
   a first arm assembly and a second arm assembly, each arm assembly including first and second reciprocating contact arms;
   the first and second arm assemblies each including a camming element, a first lever arm with a first proximal end engaged within the camming element and a first distal end engaged with the first contact arm and a second lever arm with a second proximal end engaged within the camming element and a second distal end engaged with the second contact arm, wherein when the camming element is in a first position, the first and second contact arms are urged toward each other and wherein when the camming element is in a second position, the first and second contact arms are urged away from other; and
   a drive mechanism which urges the camming element from the first position to the second position, the drive mechanism being separated from the camming element.

2. The extensometer of claim 1 wherein each arm assembly further includes a first pivot point between the first proximal end and the first distal end; and a second pivot point between the second proximal end and the second distal end.

3. The extensometer of claim 2 wherein each arm assembly further includes a support member upon which the first and second pivot points are pivotably mounted and wherein each support member includes a first end to which a proximal end of the first contact arm is resiliently flexibly mounted, and a second end to which a proximal end of the second contact arm is resiliently flexibly mounted.

4. The extensometer of claim 3 wherein the camming element is a wedge with first and second inclined camming slots, wherein the first proximal end of the first lever arm is engaged within the first inclined camming slot and the second proximal end of the second lever arm is engaged within the second inclined camming slot and wherein the first and second proximal ends of the respective first and second lever arms include respective first and second boss roller elements which are engaged so as to travel within the respective first and second inclined camming slots.

5. The extensometer of claim 4 wherein the first and second arm assemblies each include a spring for biasing the camming element toward the first position.

6. The extensometer of claim 5 wherein the drive mechanism includes a rotating element which rotates a spool, and wherein the extensometer further includes a belt with a first end attached to the camming element and a second end attached the spool, whereby when the rotating element is rotated, the spool rotates, thereby pulling the belt and urging the camming element from the first position to the second position.

7. The extensometer of claim 6 wherein the first and second arm assemblies ride on a track structure and wherein the first and second contact arms of the first and second arm assemblies are on a first side of the track structure and the rotating element is on the other side of the track structure.

8. The extensometer of claim 7 wherein the rotating element is a rotating bar, and wherein the rotating bar is attached to an element with edges which move in response to rotation of the rotating bar and operate a switch to indicate the desired range of motion of the rotating bar.

9. The extensometer of claim 8 wherein the element includes radially oriented edges and wherein the switch is an optical switch.

10. The extensometer of claim 9 wherein the spool is mounted on a spool bearing, the spool bearing including a cammed surface with at least one pocket, and wherein the extensometer further includes a spring-loaded mechanism for engaging the at least one pocket thereby maintaining an angular orientation of the spool.

11. An extensometer including:
    a first arm assembly and a second arm assembly, each arm assembly including a positioning element, first and second reciprocating contact arms, a first lever arm with a first proximal end engaged within the positioning element and a first distal end engaged with the first con tact arm, and a second lever arm with a second proximal end engaged within the positioning element and a second distal end engaged with the second contact arm;
    a vertical track structure upon which the first and second arm assemblies travel;
    wherein when the positioning element is in a first position, the first and second contact arms are urged toward each other and wherein when the positioning element is in a second position, the first and second contact arms are urged away from other; and
    a drive mechanism which urges the positioning element from the first position to the second position.

12. The extensometer of claim 11 wherein the drive mechanism includes a rotating element which operatively urges the positioning element from the first position to the second position.

13. The extensometer of claim 12 wherein the first and second contact arms of the first and second arm assemblies are on a first side of the vertical track structure and the rotating element is on the second side of the vertical track structure.

14. The extensometer of claim 13 further including a belt which extends from a spool on the rotating element to the positioning element and wherein the belt is mounted on at least one roller so that the belt passes from the first side to the second side of the vertical track structure.

15. The extensometer of claim 14 wherein each arm assembly further includes:
- a first pivot point between the first proximal end and the first distal end;
- a second pivot point between the second proximal end and the second distal end; and
- a support member upon which the first and second pivot points are pivotably mounted.

16. The extensometer of claim 15 wherein each support member includes a first end to which a proximal end of the first contact arm is resiliently flexibly mounted, and a second end to which a proximal end of the second contact arm is resiliently flexibly mounted.

17. The extensometer of claim 16 wherein the positioning element is a wedge with first and second inclined camming slots, wherein the first proximal end of the first lever arm is engaged within the first inclined camming slot and the second proximal end of the second lever arm is engaged within the second inclined camming slot; and wherein the first and second arm assemblies each include a spring for biasing the wedge toward the first position and wherein the first and second proximal ends of the respective first and second lever arms include respective first and second boss roller elements which are engaged so as to travel within the respective first and second inclined camming slots.

18. The extensometer of claim 17 wherein the rotating element is a rotating bar, and wherein the rotating bar is attached to an element with edges which move in response to rotation of the rotating bar and operate a switch to indicate the desired range of motion of the rotating bar.

19. The extensometer of claim 18 wherein the element includes radially oriented edges and wherein the switch is an optical switch.

20. The extensometer of claim 19 wherein the spool is mounted on a spool bearing, the spool bearing including a cammed surface with at least one pocket, and wherein the extensometer further includes a spring-loaded mechanism for engaging the at least one pocket thereby maintaining an angular orientation of the spool.

* * * * *